United States Patent
Bachmann et al.

(10) Patent No.: US 11,693,113 B2
(45) Date of Patent: Jul. 4, 2023

(54) QUANTITATIVE ULTRASOUND IMAGING BASED ON SEISMIC FULL WAVEFORM INVERSION

(71) Applicant: THE TRUSTEES OF PRINCETON UNIVERSITY, Princeton, NJ (US)

(72) Inventors: Etienne Bachmann, Trenton, NJ (US); Jeroen Tromp, Princeton, NJ (US); Gregory L. Davies, New York, NY (US); Daniel Steingart, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 474 days.

(21) Appl. No.: 16/643,321

(22) PCT Filed: Aug. 30, 2018

(86) PCT No.: PCT/US2018/048795
§ 371 (c)(1),
(2) Date: Feb. 28, 2020

(87) PCT Pub. No.: WO2019/046550
PCT Pub. Date: Mar. 7, 2019

(65) Prior Publication Data
US 2021/0080573 A1    Mar. 18, 2021

Related U.S. Application Data

(60) Provisional application No. 62/583,849, filed on Nov. 9, 2017, provisional application No. 62/553,257, filed on Sep. 1, 2017.

(51) Int. Cl.
*A61B 5/00*    (2006.01)
*G01N 29/06*   (2006.01)
(Continued)

(52) U.S. Cl.
CPC ........... *G01S 15/8993* (2013.01); *A61B 5/00* (2013.01); *G01N 29/0654* (2013.01);
(Continued)

(58) Field of Classification Search
None
See application file for complete search history.

(56) References Cited

U.S. PATENT DOCUMENTS

| 4,317,369 A | 3/1982 | Johnson |
| 2012/0316850 A1* | 12/2012 | Liu ........................ G01V 1/302 703/6 |

(Continued)

FOREIGN PATENT DOCUMENTS

CN    106037795 A    10/2016

OTHER PUBLICATIONS

Perez-Liva et al., "Time domain reconstruction of sound speed and reconstruction in ultrasound computed tomography using full wae inversion," J. Acoust. Soc. Am. (2017); 141(3):1595-1604.
(Continued)

Primary Examiner — Soo Shin
(74) Attorney, Agent, or Firm — Fox Rothschild LLP

(57) ABSTRACT

This disclosure provides a system and method for producing ultrasound images based on Full Waveform Inversion (FWI). The system captures acoustic/(an)elastic waves transmitted through and reflected and/or diffracted from a medium. The system performs an FWI process in a time domain in conjunction with an accurate wave propagation solver. The system produces 3D maps of physical parameters that control wave propagation, such as shear and compressional wavespeeds, mass density, attenuation, Poisson's ratio, bulk and shear moduli, impedance, and even the fourth-order elastic tensor containing up to 21 independent (Continued)

parameters, which are of significant diagnostic value, e.g., for medical imaging and non-destructive testing.

32 Claims, 8 Drawing Sheets

(51) Int. Cl.
    *G01N 29/26*     (2006.01)
    *G01N 29/34*     (2006.01)
    *G01N 29/44*     (2006.01)
    *G01S 15/89*     (2006.01)
    *G01S 7/52*     (2006.01)

(52) U.S. Cl.
    CPC ........ *G01N 29/348* (2013.01); *G01S 7/52003* (2013.01); *G06T 2200/08* (2013.01)

(56) References Cited

U.S. PATENT DOCUMENTS

| | | | | |
|---|---|---|---|---|
| 2013/0197877 | A1* | 8/2013 | Lu | G01V 99/00 703/2 |
| 2013/0245954 | A1* | 9/2013 | Shin | G01V 1/003 702/14 |
| 2014/0364735 | A1* | 12/2014 | Huang | A61B 8/5207 600/447 |
| 2019/0328355 | A1* | 10/2019 | Calderon Agudo | A61B 6/032 |
| 2022/0257217 | A1* | 8/2022 | Tai | A61B 8/4477 |

OTHER PUBLICATIONS

Palmer, P.E.S., Manual of Diagnostic Ultrasound, i-xv, 3, 11, 1995, WHO, Geneva.†

Roy, O., Sound Speed Estimation UsingWave-based Ultrasound Tomography:Theory and GPU Implementation, 76290J-1-76290J-12, 2010, Audiovisual Communications Laboratory, Ecole Polytechnique F'ed'erale de Lausanne,CH-1015 Switzerland.†

Nebeker, Jakob, Imaging of Sound Speed Using Reflection Ultrasound Tomography, 1389-1404, 2012, J Ultrasound Med.†

Bernard, Ultrasonic computed tomography based on full-waveform inversion for bone quantitative imaging, 7011-7035, 2017, Phys. Med. Biol.†

Ylitalo, Juha, Ultrasonic Reflection Mode Computed Tomography Through a Skullbone, 1059-1066, Nov. 1990, IEEE Transactions on Biomedical imaging.†

Kung Want et al. "Waveform Inversion With Source Encoding for Breast Sound Speed Reconstruction in Ultrasound Computed Tomography" Mar. 2015.†

A.V. Goncharsky et al. "A computer simulation study of soft tissue characterization using low-frequency ultrasonic tomography" 2016.†

Robert Seidl and Ernst Rank "Full waveform inversion for ultrasonic flaw identification" Feb. 16, 2017.‡

Simon Bernard et al. "Ultrasonic computed tomography based on full-waveform inversion for bone quantitative imaging" Mar. 30, 2017.†

Jing Rao et al. "Guided Wave Tomography Based on Full Waveform Inversion" May 2016.†

Farnoush Forghani-Arani et al. "High Resolution Acoustic Imaging of Laboratory Rock Samples Using Full Waveform Inversion" 2017.†

\* cited by examiner
† cited by third party

QUANTITATIVE ULTRASOUND IMAGING BASED ON SEISMIC FULL WAVEFORM INVERSION

CROSS-REFERENCE TO RELATED APPLICATIONS

This patent document claims priority under 35 U.S.C. § 119(e) to the U.S. Provisional Patent Application No. 62/553,257, filed Sep. 1, 2017, and to the U.S. Provisional Patent Application No. 62/583,849, filed Nov. 9, 2017. Each patent application identified above is incorporated here by reference in its entirety to provide continuity of disclosure.

FIELD OF THE INVENTION

The present invention relates generally to imaging systems and more specifically to quantitative ultrasound imaging systems based on seismic Full Waveform Inversion (FWI).

BACKGROUND OF THE INVENTION

The following is a discussion of relevant art pertaining to imaging systems. The discussion is not meant to be complete and is provided only for understanding of the invention that follows. The summary is not an admission that any of the work described below is prior art to the claimed invention.

Ultrasonic waves are commonly used to image media nontransparent to light. Most current applications rely on the sonographic principle, which involves sending a wave from a transducer array and recording echoes generated inside the medium using the same transducer array. For example, B-mode techniques seek to identify the time delay of the echoes from internal interfaces or scatterers in the unknown medium. The density of transducers contained in current medical ultrasound scanners contributes to making this approach viable, utilizing the delay-and-sum properties of the device. The total focusing method (TFM) is considered as one of the most accurate techniques. However, it relies on synthetic focusing of the source on each point of the medium. Another drawback is that these methods not provide any guarantee with respect to actual distances between two points in the medium, because the wavespeeds are unknown. In addition, the brightness of the picture simply reveals interfaces or scatterer density. The exact value of the pixel illumination cannot be physically interpreted, despite corrections with time gain control. Finally, the use of reflected waves at high frequencies generates speckle, which can be useful for some applications but leads to a noisy picture. To remove these artifacts, additional treatments, such as filtering or segmentation, are required, which make physical interpretation of the resulting picture more difficult. These challenges probably explain why techniques such as MRI or X-Ray imaging are preferred when a picture of higher quality is required.

Quantitative ultrasound imaging herein refers to the description of the medium as a function of physical parameters influencing acoustic waves. It is different from Quantitative UltraSound (QUS), as used in medical literature, which refers to the mean value of the considered parameters (e.g., speed of sound or attenuation). Elastography is one of quantitative ultrasound imaging techniques used to estimate Young's modulus. Acoustic radiation force impulse imaging (ARFI) elastography, for example, determines a time resolution via ultrasound speckle tracking by inducing a tissue displacement at a focal spot. Although rich information may be acquired to recover an elasticity map, it has been repeatedly reported for suffered performance on measurement reproducibility and operator dependence.

Diffraction tomography is another quantitative ultrasound imaging technique. It relies on an analogy with the X-Ray imaging method, which uses transmitted waves and the Fourier projection-slice theorem. The X-Ray frequencies and related wavelengths, which enable the use of a geometrical approximation of wave propagation, are impermissible for ultrasound since diffraction effects cannot be neglected. Further, a significant number of data acquisitions is required to obtain convincing experimental results, making it difficult to use in practice. Accordingly, there remains a pressing need for quantitative ultrasound imaging systems to overcome the challenges.

SUMMARY THE INVENTION

This disclosure provides a Full Waveform Inversion (FWI)-based method and system for producing ultrasound images. The method features an accurate wave propagation solver, which permits reconstruction of high-quality 2D and 3D computerized maps of mechanical parameters, such as compressional and shear wavespeeds, mass density, attenuation, Poisson's ratio, bulk and shear moduli, impedance, and the fourth-order elastic tensor containing up to 21 independent parameters.

The FWI-based quantitative imaging system may include a transmitting element, configured to emit a signal having a special band of frequencies, specified by a priori knowledge of a medium and an image reconstruction algorithm. The transmitting element may have a precisely known and controlled location within the system. The system further includes a receiving element, configured to capture acoustic or (an)elastic waves. The acoustic or (an)elastic waves may include those emitted by the transmitting element and/or those transmitted through and reflected from the medium. The receiving element has a small lateral extent and a precisely known and controlled location within the system. The system also includes a processor and a non-transitory computer readable medium containing programming instructions that, when executed, cause the processor to: (1) convert the captured acoustic or (an)elastic waves into observed imaging data; (2) perform an FWI process in the time domain on the observed imaging data against synthesized data. The synthesized data may be derived from a simulated model of the observed imaging data using an accurate wave propagation solver; (3) use the synthesized data to generate image representations of the medium; and (4) store and/or display the image representations of the medium.

In performing the FWI process, the system may: (i) provide an initial physical model; (ii) determine the synthesized data, by a computer, by simulating wave propagation through the physical model; (iii) back-propagate adjoint source terms determined by a cost function based on a comparison of the synthesized data and the converted acoustic or (an)elastic wave data to update the physical model; and (iv) repeat (ii) and (iii) until the residual between the synthesized data and the converted acoustic or (an)elastic wave data is less than a predetermined threshold.

In some embodiments, the system may further include one or more additional receiving elements located at a different position from the transmitting element, configured to capture the acoustic or (an)elastic waves that are transmitted through the medium.

The system may perform three-dimensional acoustic or viscoacoustic simulations. Alternatively, the system may perform three-dimensional elastic or anelastic simulations. In some embodiments, the system may invert low-frequency content of the observed imaging data, followed by progressively adding higher frequency content of the observed imaging data. In some embodiments, the system may smooth the simulated model, for example, by a Gaussian smoothing process.

In some embodiments, the system may generate the image representation, such as a physical three-dimensional model, of the medium (e.g., human tissue or non-human object). The medium may be immersed in a liquid (e.g., water).

In another aspect, this disclosure also provides a method for producing ultrasound images. The method includes: (1) emitting, by a transmitting element, a signal having a special band of frequencies, specified by a priori knowledge of a medium and the image reconstruction algorithm. The transmitting element has a precisely known and controlled location within a system; (2) capturing, by a receiving element, acoustic or (an)elastic waves that are emitted by the transmitting element and that are transmitted through and reflected from the medium. The receiving element has a small lateral extent and a precisely known and controlled location within the system; (3) converting the captured acoustic or (an)elastic waves into observed imaging data; (4) performing a FWI process in the time domain on the observed imaging data against synthesized data. The synthesized data may be derived from a simulated model of the observed imaging data using an accurate wave propagation solver; (5) using the synthesized data to generate image representations of the medium; and (6) storing or displaying image representations of the medium.

In performing the FWI process, the method may further include performing three-dimensional acoustic or viscoacoustic simulations. The FWI process may include performing three-dimensional elastic or anelastic simulations. The FWI process may include inverting low-frequency content of the observed imaging data, followed by progressively adding higher frequency content of the observed imaging data.

The method may include smoothing the simulated model, for example, by a Gaussian smoothing process. The method may include generating an image representation of the medium, which may be a human tissue or organ (e.g., bone, soft tissue). The method may include generating an image representation of the medium, which may be an object (e.g., metallic, ceramic, polymeric, welded, manufactured parts, etc.) being non-destructively tested (NDT) for quality assurance/quality control (QA/QC) or measurement purposes. The method may further include generating a physical three-dimensional model of the medium. The method may include submerging the object in a liquid, such as water.

The FWI process may further include (i) providing an initial physical model; (ii) determining the synthesized data, by a computer, by simulating wave propagation through the physical model; and (iii) back-propagating adjoint source terms determined by a cost function, based on a comparison of the synthesized data and the converted acoustic wave data to update the physical model. The method may continue with repeating (ii) and (iii) until the residual between the synthesized data and the converted wave data is less than a predetermined threshold. The cost function may be a waveform cost function. An expression of the waveform cost function for the acoustic case may include:

$$F_W(m) = \frac{1}{2} \sum_{r=1}^{N_{rec}} \int_0^T |p_{obs}(x_r, t) - p_{syn}(x_r, t, m)|^2 dt,$$

wherein $F_W(m)$ is a sum of the residuals between the synthesized data, $p_{syn}(x_r, t, m)$, and the converted acoustic wave data, $p_{obs}(x_r, t)$, over $N_{rec}$ number of the receiving transducers r at $x_r$, over a time window T, wherein m are the maps of selected parameters.

In the case of converted (an)elastic wave data, the problem is formulated as follow:

$$F_W(m) = \frac{1}{2} \sum_{r=1}^{N_{rec}} \int_0^T |s_{obs}(x_r, t) - s_{syn}(x_r, t, m)|^2 dt$$

where the term $s_{obs}(x_r, t)$ may represent the particular displacement/velocity/acceleration.

The cost function may be an instantaneous phase (IP) cost function. An expression of the instantaneous phase cost function may include:

$$F_{IP}(m) = \frac{1}{2} \sum_{r=1}^{N_{rec}} \int_0^T |\psi_{obs}(x_r, t) - \psi_{syn}(x_r, t, m)|^2 dt,$$

wherein $F_{IP}(m)$ is a sum of the residuals between the IP of synthesized data, $\psi_{syn}(x_r, t, m)$, and the IP of converted acoustic or elastic wave data, $\psi_{obs}(x_r, t)$, over $N_{rec}$ number of the receiving transducers r at $x_r$, over a time window T, wherein m are the maps of selected parameters.

The cost function may be a double difference (DD) cost function. In the acoustic FWI, an expression of the double difference cost function including:

$$F_{DD}(m) = \frac{1}{2} \sum_{i=1}^{N_{rec}} \sum_{j>i}^{N_{rec}} |\Delta t_{ij}(s_{obs}) - \Delta t_{ij}(s_{syn}(m))|^2$$

wherein $F_{DD}(m)$ is a sum of the residuals between the synthetic time of flight difference $\Delta t_{ij}(p_{syn}(m))$, and the converted acoustic wave data time of flight difference $\Delta t_{ij}(p_{obs})$, between each pair from the $N_{rec}$ receiving transducers, wherein m are the maps of selected parameters.

In the elastic FWI, an expression of the corresponding double difference cost function may include:

$$F_{DD}(m) = \frac{1}{2} \sum_{i=1}^{N_{rec}} \sum_{j>i}^{N_{rec}} |\Delta t_{ij}(s_{obs}) - \Delta t_{ij}(s_{syn}(m))|^2$$

The cost function may be a hybrid cost function, an expression of the hybrid cost function may include:

$$F_H(m) = \alpha F_T(m) + \beta F_{DD}(m) + \gamma F_{IP}(m) + \delta F_W(m),$$

wherein $F_T(m)$ is the traveltime cost function, $F_W(m)$ is the waveform cost function, $F_{IP}(m)$ is the instantaneous phase cost function, and $F_{DD}(m)$ is the double difference cost function, wherein $\alpha$, $\beta$, $\gamma$ and $\delta$ are weights of $F_T(m)$, $F_{DD}(m)$, $F_{IP}(m)$ and $F_W(m)$, respectively.

The foregoing and other objects, features, and advantages of the present disclosure set forth herein will be apparent from the following description of particular embodiments of those inventive concepts, as illustrated in the accompanying drawings. The drawings depict only typical embodiments of the present disclosure and, therefore, are not to be considered limiting in scope.

DETAILED DESCRIPTION OF THE INVENTION

Figure 1:
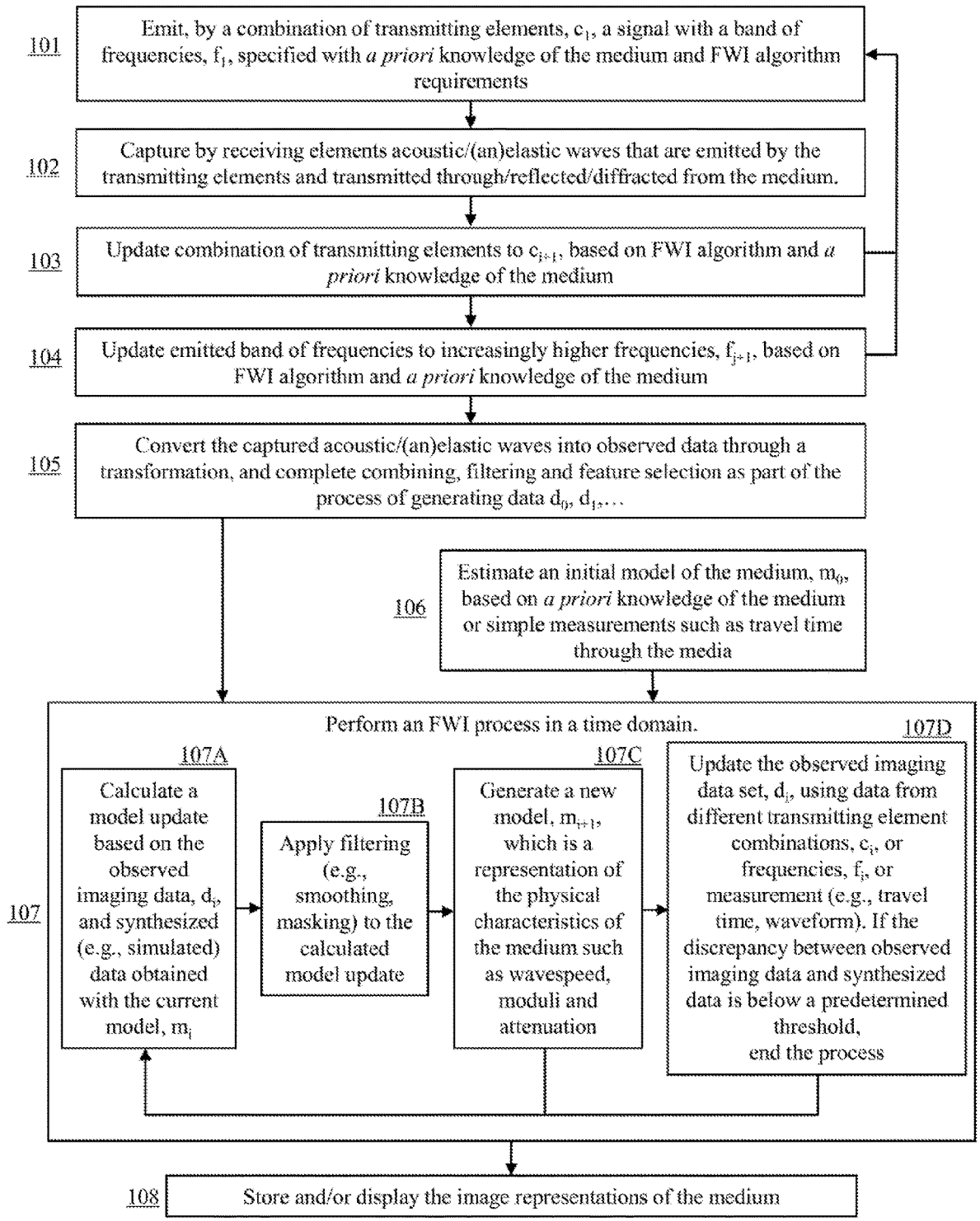
FIG. 1 shows a flow diagram of an example of an FWI-based quantitative ultrasound method.

This disclosure provides a Full Waveform Inversion (FWI)-based method and system for producing ultrasound images. The method features an accurate wave propagation solver, which permits reconstruction of high-quality 2D and 3D computerized maps of mechanical parameters, including compressional and shear wavespeeds, mass density, attenuation, Poisson's ratio, bulk and shear moduli, impedance, and the fourth-order elastic tensor containing up to 21 independent parameters.

Unlike current ultrasound imaging techniques that rely on a 2D display of recorded echoes of a wave sent from a transducer array to provide a quick qualitative image of the medium, the present method provides a quantitative 3D ultrasound imaging technique based on seismic FWI. The FWI process is performed in the time domain on the observed data against synthesized data. The synthesized data are derived from a simulated model obtained using an accurate wave propagation solver. During the FWI process, a 3D physical model of the medium is constructed by iteratively reducing differences between observations and physics-based numerical simulations using partial-differential-equation constrained optimization. The present method also produces 3D maps of physical parameters that control wave propagation, such as shear and compressional wavespeeds, which are of significant diagnostic value, e.g., for medical imaging and non-destructive testing (NDT). Because the present method only requires several ultrasound shots, FWI can be performed with an explicit time domain scheme, using minimal computing hardware resources. It also allows for including the full physics of the wave propagation, such as diffraction and reflected waves in viscoacoustic or anelastic media, to increase the accuracy of the synthesized data.

The disclosed invention differs from so-called UsCT (Ultrasound Computed Tomography) scanners that emerged in the late 2000s. UsCT features hundreds of transducers organized in a cylindrical, hemispheric, or ring shape, and are capable of performing thousands of ultrasound shots within a relatively short period of time. Most of the UsCT scanners are intended to perform reflection imaging, an extension of the conventional B-mode imaging. The geometry of the scanner has been integrated with the postprocessing signal treatment. Some of the UsCT scanners are designed for imaging breasts to detect tumors in the breasts, using purely refracted or "transmission" data. The disclosed invention is different from the UsCT methods in several aspects. First, the present system and method does not need to output thousands of ultrasound shots within minutes, as required in UsCT. This translates into a cheaper and simpler digitization system. Second, the wave propagation solver is based on time domain scheme which is solved explicitly. It permits imaging of hard objects (e.g., bones, metal) and requires only minimal computational resources. In contrast, standard UsCT are unable to image such media, because the solvers are based on frequency domain scheme that must be solved implicitly or on the parabolic approximation of the wave equation. Further, UsCT cannot accurately model 3D reflection and diffraction effects. The disclosed invention, however, can accommodate inversion of reflected waves, which contain meaningful information to properly constrain the underlying optimization problem. Due to these advantages, the present system and method is capable of providing an accurate representation of the acoustical parameter maps.

Turning now to FIG. 1, the method begins at 101 by emitting, by one or more transmitting elements or a combination of transmitting elements, $c_1$, a signal having a band of frequencies, specified by a priori knowledge of a medium and the image reconstruction algorithm (e.g., FWI algorithm requirements). The transmitting element(s) has a precisely known and controlled location within a system. At 102, the method includes capturing, by one or more receiving elements, acoustic or (an)elastic waves that are emitted by the transmitting elements. The acoustic or (an)elastic waves are transmitted through and/or reflected and/or diffracted from the medium. The receiving element(s) may have a small lateral extent and a precisely known and controlled location within the system. The receiving element(s) may be placed at the same or different position with respect to the transmitting element(s). In one example, the receiving element(s) is placed on the opposite side of the transmitting element(s).

A different transmitting element and band of frequencies may be used to acquire further data multiple times. For example, at 103, the combination of transmitting elements are updated to $c_{i+1}$ based on a predefined sequence designed to properly constrain the underlying optimization problem, and at 104, emitted band of frequencies are updated to increasingly higher frequencies, $f_{j+1}$. The method continues, at 105, with converting the captured acoustic or (an)elastic waves into observed data (e.g., imaging data) through a transformation. Combining, filtering, and feature selection is completed as part of the process of generating data $d_0$, $d_1$, . . . . At 107, the method includes performing an FWI process in the time domain on the observed imaging data against synthesized data. The synthesized data are derived from a simulated model of the observed imaging data using an accurate wave propagation solver. For the first iteration, an initial model, estimated at 106, is used. The method may include estimating an initial model of the medium, $m_0$, based on a priori knowledge of the medium or simple measurements such as travel time through the media.

At 107, an iterative process is used to update the model and generate an updated model. At the end of the process, the method may include generating image representations of the medium. During the iterative process, the method begins, at 107A, with calculating a model update based on the observed imaging data, $d_i$, and synthesized (or simulated) data obtained with the current model, $m_i$. At 107B, the method may further include applying a filtering (e.g., smoothing, masking) to the calculated model update. At 107C, the method may include generating a new model, $m_{i+1}$, which is a representation of the physical characteristics of the medium such as wavespeed, moduli, and attenuation. At 107D, the method may include updating the observed data set, $d_i$, using data from different transmitting element combinations, $c_i$, or frequencies, $f_i$, or measurement (e.g., traveltime, waveform). The method may further include ending the process, if the discrepancy between observed imaging data and synthesized data is below a predetermined threshold.

At 108, the method may include storing and/or displaying the image representations of the medium. The medium can be any object, including, without limitation, a human tissue/organ (e.g., breast, bone, soft tissue). In some embodiments, the medium is an object to be subjected to non-destructively tested (NDT) for quality assurance/quality control (QA/QC) or for measurement purposes. Such medium may include various types of materials (e.g., metallic, ceramic, polymeric, welded, manufactured parts).

In performing the FWI process, the system may (i) provide an initial physical model; (ii) determine the synthesized data by simulating wave propagation through the physical model; (iii) back-propagate adjoint source terms determined by a cost function based on a comparison of the synthesized data and the converted acoustic or (an)elastic wave data to update the physical model; and (iv) repeat (ii) and (iii) until the residual between the synthesized data and the converted acoustic or (an)elastic wave data is less than a predetermined threshold.

As described above, a priori knowledge is required to select the operating band of frequencies of the system. In conventional B-mode imaging ultrasound systems, the operating band is chosen to be as high as possible, for consideration of signal-to-noise ratios. In the FWI approach, the level of non-linearity of the underlying optimization problem is directly proportional to the band of frequencies that is used in the experiments. If this frequency content is too high, it may be impossible to obtain an image using FWI, even with noiseless data.

In performing an FWI process with a waveform cost function, the inversion can be solved when at least a part of the frequency content of the purely refracted wavefront signatures respect the cycle skipping condition: $|t_{obs} - t_{syn}| < 1/2T$. Here, $t_{obs} - t_{syn}$ models the difference in time of flight between an observed wavefront and its synthetic model, and T represents the period of the waveforms with frequencies, F, in the data (T=1/F). The band of frequencies respecting the cycle skipping condition must be large enough to generate a wavefront that is smaller than the size of the medium being imaged. The maximum limit $F_{max}$ should be chosen depending on the computational resources available and the chosen algorithm.

In practice, this band of frequencies for FWI may be chosen depending on the a priori knowledge of the acoustical properties of the medium. The acoustical properties, such as the wavespeeds and the attenuation, directly control the time of flight, t. In consequence, it is the initial discrepancy between the numerical model of these parameters and the observed real data that drives the gap $t_{obs} - t_{syn}$. In a medical imaging context, for instance, these acoustical properties are well known for each tissue, but the dimensions and the positioning of the tissues may vary from one patient to another. Depending on these uncertainties, it is possible to determine the largest gap $t_{obs} - t_{syn}$ that may appear during the inversion, and therefore specify the relevant starting frequency.

One such method to determine the appropriate bandwidth based on some a priori knowledge is expressed in the following formula:

$$\begin{cases} F_{min} + \Delta F < \underset{i,j}{\mathrm{argmax}} \int_{x_{s_i}}^{x_{r_j}} \left| \frac{1}{c_{init}(x)} - \frac{1}{c_{init}(x) + \Delta c(x)} \right| dx \\ \frac{\overline{c_{init}}}{F_{min}} \propto L \\ \exists s(t) \text{ such that } \begin{cases} F_{min}(s(t)), F_{max}(s(t)) \in [F_{min}; F_{max} + \Delta F], \\ env(s(t))\overline{c_{init}} < L \end{cases} \end{cases}$$

where $F_{min}$ is the minimum frequency, $\Delta F$ is the width of the frequency band that respect the cycle skipping condition, $x_{s_i}$ is the position of the $i^{th}$ source, $x_{r_j}$ is the position of the $j^{th}$ receiver, $c_{init}(x)$ is the initial guess of the wavespeed at position x, $\Delta c(x)$ is the initial uncertainty about the wavespeed at position x, $\overline{c_{init}}$ is the mean of the initial guess wavespeed in the medium, L is the minimum dimension of the medium, s(t) is a pulse signal and env( ) the envelope function. It is also worth noting that accurately identifying the maximum potential wavespeed discrepancies helps to select a higher frequency band, which leads to a better resolution.

An alternate method to empirically determine the appropriate frequency bandwidth may be appropriate, when uncertainties are large, or the properties of the medium being imaged are totally unknown. In these cases, the deterministic, a priori knowledge approach may not apply, and the frequency content may be chosen with an empirical approach based on data observation, combined with a sweep in frequency. If the selected frequency band is too low, the purely refracted wavefront signatures of the observed data should look similar to the purely refracted wavefront signatures of the synthesized data. If the selected frequency band is too high, the purely refracted wavefront signatures of the observed data will be temporally located far (in terms of time of arrival) from the purely refracted wavefront signatures of the synthesized data, or may not be identifiable. When sweeping from low to high frequencies, the correct frequency to choose would be the one that starts to show visible discrepancies between observed and synthesized wavefronts, but such that the cycle skipping condition is still respected. This ensures that the observed data contains valuable information with respect to the inversion process. This approach can be automated with an algorithm.

In performing an inversion with a traveltime cost function, an empirical approach based on frequency sweeping is also possible. A priori knowledge about the medium is not necessary, but may help to reduce the selected frequency bands for the frequency sweep. A similar approach to the case using the waveform cost function may also apply. However, the traveltime approach is not limited by the cycle skipping condition. In practice, the only constraint is to make sure that purely refracted wavefront signatures remain identifiable. When increasing the frequency content, diffraction effects may affect the capability to distinguish diffracted wavefronts from refracted wavefronts, which affect the algorithm when computing the traveltime differences. This approach can also be automated with an algorithm.

The accuracy of the wave propagation solver plays an important role in algorithm convergence. Although approximate ray-based or Helmholtz equation solvers have been used by the seismic and medical imaging community due to their relatively lower computational cost, these equations and their related solvers do not accommodate the full physics of the problem, such as 3D scattering and diffraction, which leads to undesired consequences for the fidelity of the synthesized data. In contrast, in various embodiments, the present methods use an accurate wave propagation solver to ensure the accuracy of gradient calculations in the FWI process. The accurate wave propagation solver may also be used to solve the full (an)elastic wave equation, for any heterogeneous and irregular medium.

In some embodiments, the FWI process of the present method may include performing 3D acoustic or viscoacoustic simulations. Alternatively, the FWI process may include performing 3D elastic or anelastic simulations. The FWI process may also include performing 3D acoustic or viscoacoustic simulations alone or in combination with 3D elastic or anelastic simulations. The FWI process may include inverting the low-frequency content of the observed imaging data followed by progressively adding higher frequency content of the observed imaging data. In some embodiments, the method may include smoothing the simulated model, for example, by applying a Gaussian smoothing process to the simulation model.

In performing the FWI process, the method may include (i) providing an initial physical model; (ii) determining the synthesized data, by a computer, by simulating wave propagation through the physical model; (iii) back-propagating adjoint source terms determined by a cost function based on a comparison of the synthesized data and the converted acoustic wave data to update the physical model. The method may continue with repeating (ii) and (iii) until the residual between the synthesized data and the converted acoustic or (an)elastic wave data is less than a predetermined threshold.

To provide high-resolution maps of various physical properties using FWI, the requirements of system and transducer calibration for FWI are higher than conventional ultrasound systems. In order to invert for models that generate synthetic data that best fits the experimental measurements in terms of full waveforms, the systems and transducer arrays need to be characterized carefully such that no unexpected modeling errors are introduced.

There are two main aspects addressed in the invention. The first aspect is accurately modeling the physical quantities of measured data. Ultrasonic transducers convert mechanical energy into an electrical signal, and vice versa. Different types of transducers can be used, depending on the purposes of the system. In conventional ultrasound, a transducer, often composed of piezoelectric materials excited by electrical impulses, can input energy into a medium, generating propagating acoustic or (an)elastic waves, dependent on the media. In order to meaningfully compare the synthetic data with experimental measurements, correctly understanding and accurately modelling the physical attributes that a receiver measures are critical to the successful implementation of FWI. Some examples of the transducers that can be incorporated into the system are listed as follows: for an ultrasonic transducer, an electric signal acquired is induced by the integration effects of particle velocities on its front surface in an acoustic medium or the integrated strain of the piezoelectric materials in an elastic medium; for hydrophone, a signal is a direct representation of the pressure in an acoustic medium; for laser Doppler vibrometer (LDV), a signal is the surface velocity or displacement, at which the laser beam is directed, on the measured object. The SPECFEM software can accurately and efficiently model all the above quantities.

The second aspect is the geometry and positioning of the transducer array or individual transducer elements. In FWI, the receiving transducer array or element's coverage and spacing determine the usefulness of the data for inversion. The true location of the transducer arrays or elements need to be accurately represented in the simulation to prevent data misfit caused by positioning errors. The system will minimize the potential positioning errors by precise manufacturing of the device and by incorporating a self-calibrating scheme to determine the transducer array positioning in numerical simulation for stable and accurate inversion. The modeling, redesign, and alignment of the transducer array are based on decades of knowledge and experience of the applicants in FWI practices, satisfying the needs for FWI to provide high-resolution maps for various physical quantities while performing the calculation efficiently.

Figure 2:
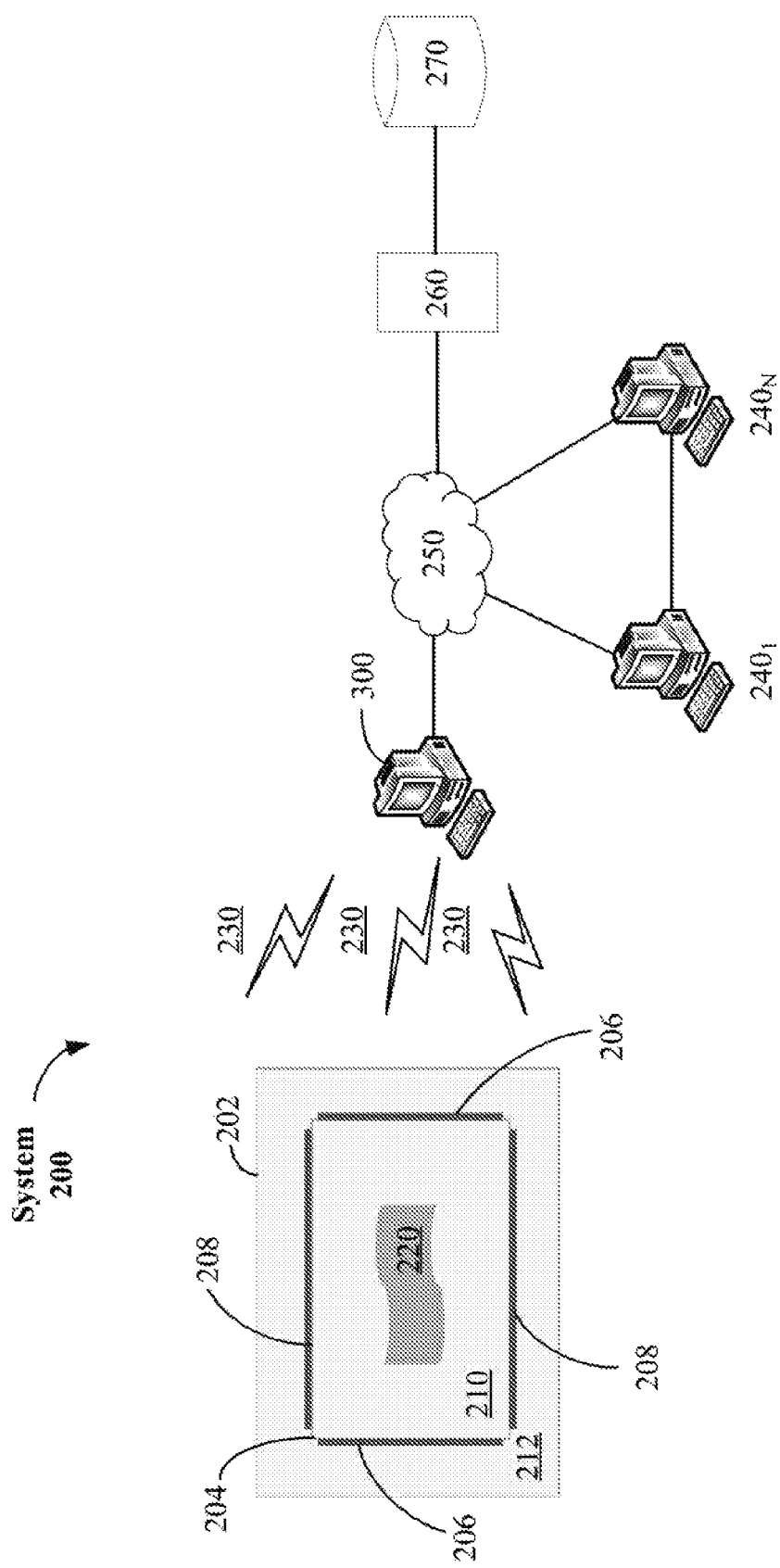
FIG. 2 shows an example of an FWI-based quantitative ultrasound system.

FIG. 2 illustrates an example of FWI-based quantitative imaging system 200 for producing ultrasound images. System 200 may include one or a plurality of transducers 206 and 208. Transducers may include one or more elements (e.g., ultrasonic elements). The transducers can be arranged to form a transducer array. The transducers may be attachable to container 204. The transducers may be independent from the container 204. The transducers may be supported by an external housing structure 202, which is independent of or attachable to container 204. The container can be made from a variety of materials, including plastics, metals, or other materials. The transducers can also be created using existing manufacturing processes. In some embodiments, the transducers may be fixed to or moveable with respect to the container 204 or each other. The transducers may be configured to interface with the container 204 and allow for a tight coupling for transmission of ultrasonic waves through the container 204, liquid, and the object to be measured. The container 204 and the transducer array comprising the transducers may be coupled with an ultrasonic pulser and/or receiver device, to send and record ultrasonic pulses.

In some embodiments, the system may further include water or other acoustically transmissive media 210 in container 204. To avoid direct liquid contact in sensitive applications, acoustically transmissive media 210 may be filled in a flexible and acoustically transmissive container (e.g., balloon), which can be inflated against an object for imaging 220. The object for imaging 220 may be immersed in acoustically transmissive media 210. In some embodiments, the system may further include external housing structure 202. The external housing structure 202 may include water or other acoustically transmissive media 212. Precisely controlled ultrasonic waveforms can be transmitted and received throughout the transducers network, in any ordering or combination as desired. The data from the transducers can be analyzed to determine the internal and external structure of the object.

The system for producing ultrasonic images may include one or more transducer elements. The attributes of both the system (i.e., the transducer geometry) and the transducer elements (i.e., the properties of independent elements) are chosen to provide the necessary inputs for the FWI process. The transducer geometry, the spatial positioning of the transducers and the operating band of frequencies of the system may differ significantly from conventional ultrasonic systems.

The transducer elements are capable of either independently or simultaneously transmitting ultrasonic pulses through the medium of interest, in any chosen element combination. Signals may also be simultaneously measured from any combination of the transducer elements, including transmitting elements. In addition, all elements are not necessarily alike. Different elements may be specified to transmit and/or receive different frequency content, allowing for progressive increases in the frequencies transmitted and measured for input into the FWI algorithm. This feature allows for successive image refinement.

The geometry of the source and receiver locations is very precise and tightly controlled. To support the FWI technique, accurate positioning of the transducer elements is critical, with tolerances required to within 10 s of microns. This is not only advantageous for generating high-resolution images, but also provides the ability to select and control specific transmit and receive transducer combinations in order to speed up the imaging algorithms through minimizing the number of "shots" required for any given image.

Unlike conventional ultrasound, having a high linear or areal density of transducer elements is not critical for the disclosed quantitative ultrasound imaging. With the FWI technique, the transducer elements may be more sparsely spaced. Therefore, transducer arrays, with multiple elements closely spaced within a single device, may not exist in the traditional sense of the word for this type of device. Transducer element is so placed that transmitted or reflected waves propagate through the region of interest, and are captured at receiving elements, providing comprehensive information from the complete area of interest. Full coverage of the area of interest may be achieved through translation and rotation of the elements between different "shots."

To generate 3D images, it may not be sufficient to have a single linear transducer array. Areal (2D) transducer coverage may be required to provide sufficient data for FWI inversion. This can be achieved through translation of single elements, translation of linear arrays, translation of areal (2D) arrays, with areal (2D) arrays, or with a 2D/3D coverage of elements.

The elements have several desirable characteristics to support the FWI method. For example, broadband sources can be used to provide a wide range of frequency content. This allows for filtering of specific frequency windows, facilitating image refinement as the filtered frequency is increased. In some scenarios, low frequencies may be preferred for FWI, in part, due to the cycle-skipping criterion and, in part, because full waveforms contain more information than measurement of a single wave arrival time (thus single point accuracy is less critical). This is in contrast with more conventional imaging techniques which utilize high frequencies to allow more precise arrival time determination. This is, however, not necessary for the FWI technique.

In a preferred embodiment, the lateral extent (width and height) of the receiving transducers is small, typically less than the wavelength in the transmitting medium. This is important for accurate measurement of the true waveform of wave arrivals, particularly those that strike the transducer at an oblique angle (traveling more parallel to the transducer face than perpendicular to it).

Transmitting transducers, however, need not have a small lateral extent. They may have a large surface area for sending waves which are largely planar. Multiple transmitting elements may also be simultaneously used with pre-calculated delays, providing widespread, constructive wavefronts with wide coverage and high signal-to-noise ratio.

Transducer elements may be any one of the technologies or their combinations, including, without limitation, piezoelectric transducers, capacitive micromachined ultrasonic transducers (CMUT), laser Doppler vibrometers (LDV), and the like.

In some embodiments, system 200 can be a network-based system in which computing device 300 can be deployed in some scenarios. In this network-based scenario, computing device 300 is communicatively coupled to a server 260 and other computing devices $240_1, \ldots, 240_N$ via a network 250 (e.g., the Internet or Intranet). Computing devices $240_1, \ldots, 240_N$ can be the same as, similar to, or different than computing device 300. During operation, computing devices 300, $240_1, \ldots, 240_N$ may write data to or read data from database 270. Each computing device 300, $240_1, \ldots, 240_N$ includes, but is not limited to, a robot, a three dimensional ("3D") animate, a personal computer, a laptop computer, a desktop computer, a personal digital assistant, a smartphone or any other electronic device having input and output components (e.g., a speaker, a display screen, a keypad and/or a touchscreen). In some scenarios, the present solution includes software that is at least partially installed and run on the computing device 300, computing device $240_1, \ldots, 240_N$ and/or server 260. In some scenarios, system 200 may communicate data from transducers 206 and 208 to computing device 300 via network 230. In some scenarios, the communication is a real-time communication.

Figure 3:
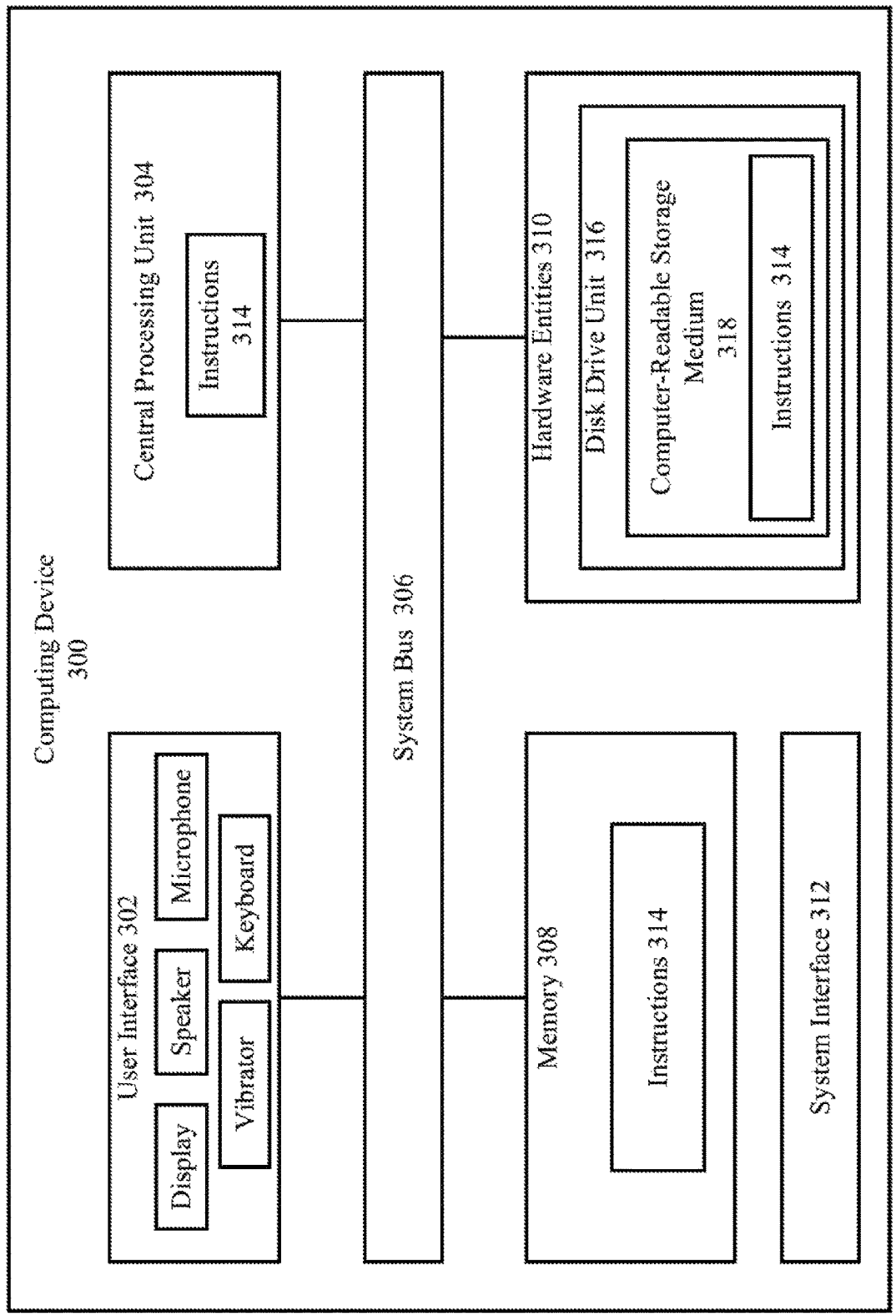
FIG. 3 shows an example of an architecture for a computing device to implement an FWI-based quantitative ultrasound method.

Referring now to FIG. 3, a computing system/device 300 is generally configured to perform operations for facilitating the connection of peripheral and central nerves output signatures of variability through the same statistical platform. As such, the computing system 300 includes a plurality of components 302-312. The computing system 300 can include more or fewer components than those shown in FIG. 3. However, the components shown are sufficient to disclose an illustrative embodiment implementing the present solution.

The hardware architecture of FIG. 3 represents one (1) embodiment of a representative computing device configured to facilitate the connection of peripheral and central nerves output signatures of variability through the same statistical platform. As such, the computing system 300 implements methods of the present solution.

The computing system 300 may include a system interface 312, a user interface 302 (e.g., a keyboard for data input and a display for data output), a Central Processing Unit ("CPU") 304, a system bus 306, a memory 308 connected to and accessible by other portions of the computing system 300 through system bus 306, and hardware entities 310 connected to system bus 306. At least some of the hardware entities 310 perform actions involving access to and use of memory 308, which can be a Random Access Memory ("RAM"), a disk driver and/or a Compact Disc Read Only Memory ("CD-ROM"). System interface 312 allows the computing system 300 to communicate directly or indirectly with external devices (e.g., transducers, servers, and client computers).

Hardware entities 310 may include microprocessors, Application Specific Integrated Circuits ("ASICs") and other hardware. Hardware entities 310 can include a microprocessor programmed to facilitate the connection of peripheral and central nerves output signatures of variability through the same statistical platform.

The hardware entities 310 may include a disk drive unit 316 including a computer-readable storage medium 318 on which is stored one or more sets of instructions 314 (e.g., software code) configured to implement one or more of the methodologies, procedures, or functions described herein. The instructions 314 can also reside, completely or at least partially, within the memory 308 and/or the CPU 304 during execution thereof by the computing system 300. The components 308 and 304 also can constitute machine-readable media. The term "machine-readable media," as used here, refers to a single medium or multiple media (e.g., a centralized or distributed database, and/or associated caches and servers) that store the one or more sets of instructions 314. The term "machine-readable media," as used here, also refers to any medium that is capable of storing, encoding or carrying a set of instructions 314 for execution by the computing system 300 and that cause the computing system 300 to perform any one or more of the methodologies of the present disclosure.

Notably, the present solution can be implemented in a single computing device as shown in FIG. 3. The present solution is not limited in this regard. Alternatively, the present solution can be implemented in a distributed network system. For example, the present solution can take advantage of multiple CPU cores over a distributed network of computing devices in a cloud or cloud-like environment. The distributed network architecture ensures that the computing time of the statistics and enhanced functionality is reduced to a minimum, allowing end-users to perform more queries and to receive reports at a faster rate. The distributed network architecture also ensures that the implementing software is ready for being deployed on an organization's internal servers or cloud services in order to take advantage of its scaling abilities (e.g., request more or fewer CPU cores dynamically as a function of the quantity of data to process or the number of parameters to evaluate).

The system provides non-invasive, low cost, and accurate imaging of objects in a simple and safe way. Unlike traditional imaging, which is either invasive, requires direct contact, or is highly expensive, the system allows for non-contact, rapid ultrasonic measurement. The measurements may include internal and external structural details of the object. In some scenarios, the object may be a human or animal subject. In some scenarios, the object may be a body part of the human or animal subject or a non-living object.

Full Waveform Inversion (FWI)

FWI is formulated as an optimization problem seeking to minimize discrepancies between observed data, $p_{obs}$, and synthetic data, $p_{syn}$, by adjusting the numerical model parameters, m, that govern the physics of wave propagation.

1) Acoustic Case

Mathematically, one defines a cost or misfit function:

$$F(m^*) = \min(F(m)) \text{ where } F(m) = \text{dist}(p_{obs}, p_{syn}) \quad (1)$$

where $m^*$ is the true model. p may represent the acoustic pressure. Equation (2) illustrates the case of a viscoacoustic medium, involving sound or pressure waves, where the attenuation is modeled by a set of L standard linear solids. The simulated "synthetic" pressure $p_{syn}$ is governed by the viscoacoustic wave equation, which is formulated in terms of a fluid potential $\Phi$. To illustrate the most general case, we choose a full parametrization $m = (\kappa, \rho, Q_\kappa)$, involving the bulk modulus $\kappa$, the mass density $\rho$ and the $\kappa$ attenuation factor $Q_\kappa$, the associated wave equation is $$\begin{cases} p_{syn} = -\partial_t^2 \Phi \\ \frac{1}{\kappa_U} \partial_t^2 \Phi = \nabla\left(\frac{1}{\rho}\nabla\Phi\right) - \sum_{l=1}^{L} \frac{R_\kappa^l}{\kappa_U} + \sum_{s=1}^{N_s} \frac{1}{\kappa_U} f_s \\ \partial_t R_\kappa^l = -\frac{R_\kappa^l}{\tau_{k\sigma}^l} + \nabla\left(\frac{1}{\rho}\nabla\Phi\right)\delta\kappa^l / \tau_{k\sigma}^l \end{cases} \quad (2)$$

with $\kappa_U$ the unrelaxed bulk modulus, where $N_s$ denotes the number of sources and $f_s$, the source term associated with source s. If effects of attenuation are negligible for a given medium, one can remove the $$\sum_{l=1}^{L} \frac{R_\kappa^l}{\kappa_U}$$

term of the second line of Eq. (2), and do not need to solve the third line of Eq. (2).

For a given modulus M (which can be here the bulk modulus $\kappa$, or in the elastic case, the shear modulus $\mu$), the modulus defect $\delta M^l$ of the $l^{th}$ standard linear solid is expressed as:

$$\delta M^l = \left(\sum_{l=1}^{L} \frac{\tau_{M_\epsilon}^l}{\tau_{M_\sigma}^l}\right)^{-1} \left(\frac{\tau_{M_\epsilon}^l}{\tau_{M_\sigma}^l} - 1\right) \quad (3)$$

The constants $\tau_{M_\sigma}^l(x)$, $\tau_{M_\epsilon}^l(x)$ are determined according to the local value of the quality factor $Q_M$. They are obtained solving an optimization problem such that, over a given frequency range that includes the frequency range of interest for the wave propagation:

$$\frac{1}{Q_M} \approx \frac{\sum_{l=1}^{L} \frac{\omega(\tau_{M_\sigma}^l - \tau_{M_\epsilon}^l)}{1+\omega^2 \tau_{M_\sigma}^{l2}}}{\sum_{l=1}^{L} \frac{1+\omega^2 \tau_{M_\sigma}^l \tau_{M_\epsilon}^l}{1+\omega^2 \tau_{M_\sigma}^{l2}}} \quad (4)$$

To obtain the derivative of the cost function F with respect to the parameterization m, the adjoint state method is used. This derivative may be expressed as follows, in the acoustic FWI:

$$\delta F = \int_\Omega (\delta \ln \rho^{-1} K_\rho + \delta \ln \kappa^{-1} K_\kappa + \delta Q_\kappa^{-1} K_{Q_\kappa^{-1}}) d\Omega \quad (5)$$

where $\Omega$ denotes the model volume, and where the notation $\delta \ln$ $$m_i^{-1} = -\frac{\delta m_i}{m_i}$$

is used. The sensitivity kernels or Fréchet derivatives are also introduced:

$$\begin{cases} K_\kappa(x) = -\int_0^T \kappa^{-1}(x) \partial_t \Phi_1^\dagger(x, T-t) \partial_t \Phi(x, t) dt \\ K_\rho(x) = -\int_0^T \rho^{-1}(x) \nabla \Phi_1^\dagger(x, T-t) \cdot \nabla \Phi(x, t) dt \\ K_{Q_\kappa^{-1}}(x) = -\int_0^T \kappa^{-1}(x) \partial_t \Phi_2^\dagger(x, T-t) \partial_t \Phi(x, t) dt \end{cases} \quad (6)$$

For problems that do not show significant effects of mass density (or attenuation), the term $K_\rho(x)$ (or $K_{Q_\kappa^{-1}}(x)$ resp.) can be ignored. In equation (6) spatial and temporal dependencies are explicitly shown. Note that calculation of the kernels involves a temporal convolution of the forward and adjoint wavefields. Here $\Phi$ denotes the forward wavefield representing wave propagation during the experiment. The adjoint wavefields $\Phi_1^\dagger$ and $\Phi_2^\dagger$ are also governed by the viscoacoustic wave equation (2), but have different source terms, respectively noted $f_1$ and $f_2$. For a viscoacoustic least-squares waveform misfit function, these source terms involve the time-reversed difference between observed and synthetic data simultaneously injected at the location $x_r$ of the receivers $r=1, \ldots, N_r$:

$$\begin{cases} \forall r \in [\![1; N_r]\!], f(x_r, t) = \partial_{t^2} [p_{obs}(x_r, T-t) - p_{syn}(x_r, T-t)] \delta(x-x_r) \\ f_1(t) = \sum_{r=1}^{N_r} f(x_r, t) \\ f_2(t) = \sum_{r=1}^{N_r} ifft\left(\left[\frac{2}{\pi}\ln\left(\frac{|\omega|}{\omega_0}\right) - i\,sgn(\omega)\right] fft(f(x_r, t))\right) \end{cases} \quad (7)$$

where fft and ifft denote the Fourier transform and its inverse, and $\omega_0$ is the frequency of reference of the bulk modulus.

The expressions for the kernels $K_\kappa(x)$, $K_\rho(x)$ and $K_{Q_\kappa^{-1}}(x)$ in equation (6) are instructive, because they show how local variations in $\kappa$ or $\rho$ influence recorded data. Since the computation of $K_\kappa(x)$, $K_\rho(x)$ and $K_{Q_\kappa^{-1}}(x)$ requires three wavefield simulations, the computational cost is non-negligible and requires the use of local optimization techniques, despite the non-convexity of the problem. Usual techniques such as steepest descent or (quasi-) Newton methods can be used. To speed-up convergence, the seismic community often favors the use of the Limited-Memory Broyden-Fletcher-Goldfarb-Shanno (L-BFGS) method, which is a quasi-Newton method that avoids assembly of the full Hessian.

2) Elastic Case

The misfit function writes $$F(m^*) = \min(F(m)) \text{ where } F(m) = dist(s_{obs}, s_{syn}) \quad (9)$$

where s may represent the particular displacement, velocity or acceleration. We consider in the anelastic case the parameterization $m = (\kappa, \mu, \rho, Q_\kappa, Q_\mu)$.

a) Isotropic Case

For an anelastic medium, wave propagation may be modeled by the following set of equations:

$$\begin{cases} \rho \partial_t^2 s = \nabla \cdot T + f \\ T = \kappa_U tr(\epsilon)I + 2\mu_U d - \sum_{l=1}^L R_\kappa^l I - \sum_{l=1}^L R_\mu^l \\ \varepsilon = \frac{1}{2}[\nabla s + (\nabla s)^T] \\ d = \epsilon - \frac{1}{3} tr(\epsilon) \\ \partial_t R_\kappa^l = -\frac{R_\kappa^l}{\tau_{\kappa_\sigma}^l} + \frac{tr(\epsilon)\delta\kappa^l}{\tau_{\kappa_\sigma}^l} \\ \partial_t R_\mu^l = -\frac{R_\mu^l}{\tau_{\mu_\sigma}^l} + \frac{d\,\delta\mu^l}{\tau_{\mu_\sigma}^l} \end{cases} \quad (10)$$

Where s denotes the particular displacement, $\varepsilon$ the infinitesimal strain tensor, d the strain deviator, f the source term, $\kappa_U$ the unrelaxed bulk modulus and $\mu_U$ the unrelaxed shear modulus. The constants $\tau_{\kappa_\sigma}^l$, $\tau_{\kappa_\epsilon}^l$, $\tau_{\mu_\sigma}^l$, and $\tau_{\mu_\epsilon}^l$ are, as for the viscoacoustic FWI, determined by solving an optimization problem such that Eq. (4) applies over the frequency range of interest of the wave propagation. The modulus defects $\delta\kappa^l$ and $\delta\mu^l$ are defined following Eq. (3).

In various media, the $\kappa$ attenuation is not significant, which leads here to remove the $\Sigma_{l=1}^L R_\kappa^l I$ term in Eq. (10). Similarly, when $\mu$ attenuation is negligible, one can remove the $\Sigma_{l=1}^L R_\mu^l I$ term in Eq. (10).

The derivative of the cost function F with the parameterization $m = (\kappa, \mu, \rho, Q_\kappa, Q_\mu)$ is:

$$\delta F = \int_\Omega (\delta \ln \rho K_\rho + \delta \ln \kappa K_\kappa + \delta \ln \mu K_\mu + \delta Q_\kappa^{-1} K_{Q_\kappa^{-1}} + \delta Q_\mu^{-1} K_{Q_\mu^{-1}}) d\Omega \quad (11)$$

with the corresponding sensitivity kernels:

$$\begin{cases} K_\rho(x) = -\int_0^T \rho(x) s_1^\dagger(x, T-t) \partial_{t^2} s(x, t) dt \\ K_\kappa(x) = -\int_0^T \kappa(x)[\nabla \cdot s_1^\dagger(x, T-t)][\nabla \cdot s(x, T-t)] dt \\ K_\mu(x) = -\int_0^T 2\mu(x) d_1^\dagger(x, T-t) : d(x, t) dt \\ K_{Q_\kappa^{-1}}(x) = -\int_0^T \kappa(x)[\nabla \cdot s_2^\dagger(x, T-t)][\nabla \cdot s(x, T-t)] dt \\ K_{Q_\mu^{-1}}(x) = -\int_0^T 2\mu(x) d_2^\dagger(x, T-t) : d(x, t) dt \end{cases} \quad (12)$$

Here s denotes the forward wavefield representing wave propagation during the experiment, and d is the corresponding traceless strain deviator. The adjoint wavefields $s_1^\dagger$ and $s_2^\dagger$ and their corresponding traceless strain deviators $d_1^\dagger$ and $d_2^\dagger$ are also governed by the anelastic wave equation (10), but have different source terms, respectively noted $f_1$ and $f_2$.

For an anelastic least-squares waveform misfit function, these source terms involve the time-reversed difference between observed and synthetic data simultaneously injected at the location $x_r$ of the receivers $r=1, \ldots, N_r$:

$$\begin{cases} \forall r \in [\![1; N_r]\!], f(x_r, t) = [s_{obs}(x_r, T-t) - s_{syn}(x_r, T-t)]\delta(x-x_r) \\ f_1(t) = \sum_{r=1}^{N_r} f(x_r, t) \\ f_2(t) = \sum_{r=1}^{N_r} ifft\left(\left[\frac{2}{\pi}\ln\left(\frac{|\omega|}{\omega_0}\right) - i\,\text{sgn}(\omega)\right] fft(f(x_r, t))\right) \end{cases} \quad (13)$$

b) Anisotropic Case

Some media, such as bones or composite materials, demonstrate anisotropic properties that have a significant effect on wave propagation. In bones, the shear wavespeed or the compressional wavespeed can double depending on the direction of propagation. Composite materials can also display strong angle-dependence of wavespeed. In this case, we consider the wave equation that features a fourth-order elastic tensor c, to take into account anisotropy:

$$\begin{cases} \rho \partial_t^2 s = \nabla \cdot T + f \\ T = c : \epsilon \\ \varepsilon = \frac{1}{2}[\nabla s + (\nabla s)^T] \end{cases} \quad (14)$$

We assume now $m = c_{ijkl}$, where $c_{ijkl}$ is one component of the elastic tensor. We have:

$$\delta F = \int_\Omega \delta \ln c_{ijkl} K_{ijkl} d\Omega \quad (15)$$

With:

$$K_{c_{ijkl}}(x) = -\int_0^T c_{ijkl}(x)\,\epsilon^\dagger_{jk}(x, T-t)\epsilon_{lm}(x, t)dt \quad (16)$$

To minimize the risk of being trapped in a local minimum of the cost function, a regularization procedure is often added to the iterative process, which consists of smoothing the calculated gradient. Various regularization approaches exist and have been applied to geophysical Full Waveform Inversion, for instance using the Laplacian norm of the model, Tikhonov regularization, or the total variation method. In the numerical experiments, a Gaussian smoothing to the gradient K is applied, using only points located in the vicinity $\Gamma$ of point x, in order to minimize the computational burden. Mathematically, $$\hat{K}(x) = \frac{\int_\Gamma K(x')\exp\left[-\frac{(x-x')^2}{2\sigma^2}\right]d^3x'}{\int_\Gamma \exp\left[-\frac{(x-x')^2}{2\sigma^2}\right]d^3x'} \quad (17)$$

Usually, $\Gamma$ is a disk centered on x with a radius large enough to compute at least 99% of the theoretical value of $$\int_{-\infty}^{+\infty} \exp\left[-\frac{(x')^2}{2\sigma^2}\right]d^3x'$$

which is $\sqrt{2\pi\sigma}$. The control parameter $\sigma$, which defines the smoothing strength, permits a simple adaptation to the dimensions of the medium.

As with all non-convex problems treated with local optimization tools, some knowledge of the underlying physics and specific techniques are necessary to avoid being trapped in a local minimum of the cost function. Referring to the geophysics literature, a strategy can be to first invert the low-frequency content of the data, and subsequently add increasingly higher frequencies over the iterations to improve resolution. Another strategy is to aim for a wide aperture between the source of the wave, a point in the medium, and the recording point. This enables reconstruction of large structures in the medium, which must be recovered first to avoid being trapped in a local minimum. A good strategy is to maximize this aperture in order to record transmitted waves, which is the case when the recording point is located behind the medium with respect to the source. In exploration geophysics, such a setup is impossible for deep geological structures, because receivers cannot easily be buried deeply nor located underneath the target. In a conventional echography setup, the same transducer array is used to emit and record waves, which leads to a small aperture. Nevertheless, many ultrasound imaging applications could accommodate the use of a second transducer array placed behind the medium, which allows one to record transmitted waves. This leads to an experimental setup in which at least two transducer arrays for numerical experiments are used.

In the particular case of inversions involving a waveform cost function, a necessary condition with respect to convergence has to be respected, namely the cycle-skipping condition. It implies that the time of flight difference between observed and synthetic waves has to be less than half the period of the wave. If not, the inversion process might get stuck in a local minimum.

Ultrasound FWI Procedures

Wave Propagation Solver

As mentioned above, an accurate model of wave propagation is necessary to correctly evaluate the misfit function. This may be achieved using numerical methods, such as finite differences, finite elements or spectral elements, but this comes at a considerable computational cost, especially in 3D. To mitigate this computational burden, an explicit time marching scheme is preferred. Usually, implicit schemes are preferred when: (1) Hundreds of wave simulations in the same medium are used; and (2) the solution does not need to be known in various timesteps (for time-domain solvers)/frequencies (for frequency domain solvers)

In the FWI context, these advantages are not a necessity. It is possible to constrain properly the corresponding optimization problem using only a small number of wave emissions in the medium. Additionally, the accurate evaluation of the sensitivity kernels, which are formulated with an integral over time or frequency requires an important number of evaluation points. This also mitigates one drawback of the explicit time scheme, namely, the conditional stability. Finally, it is difficult to overcome the main drawbacks of the implicit scheme, which include the computational cost of the inversion of the mass matrix, its lower-upper factorization (or LU factorization), and the associated hardware requirements in terms of memory. These drawbacks cannot be solved using larger clusters or supercomputers, because the implicit formulation requires "all-to-all" communications, which considerably slow down the calculations. On the other hand, the employed explicit schemes used in the disclosed system can be scaled on large machines and do not require any matrix inversion. The matrix does not even need to be assembled, which drastically reduces the memory requirements.

A GPU Acceleration

Figure 4:
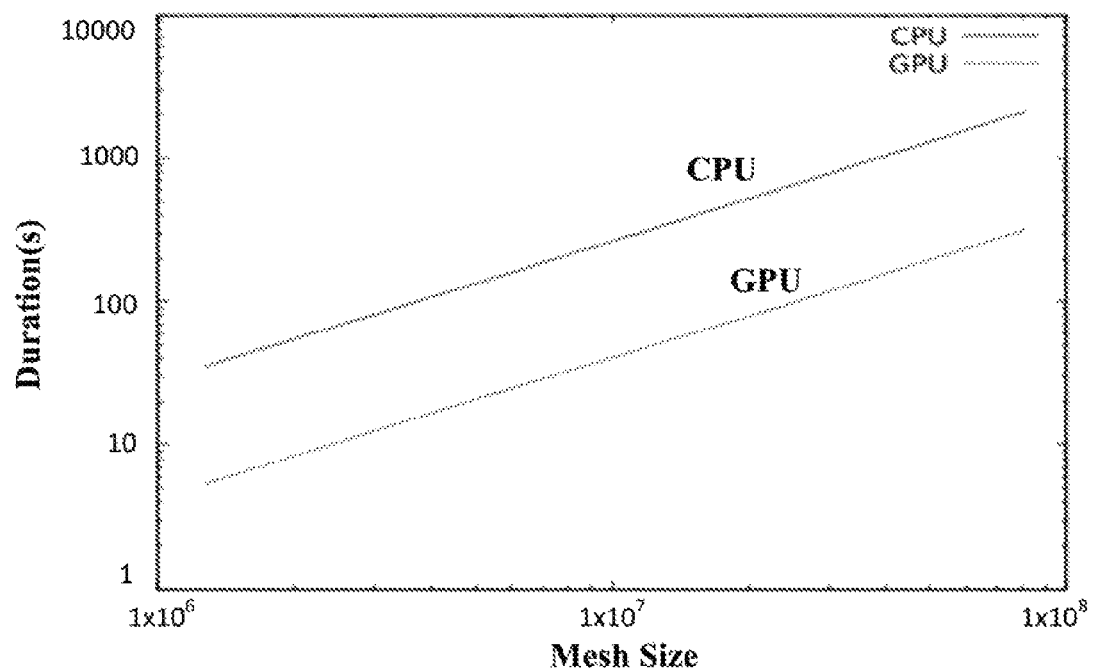
FIG. 4 shows a comparison between CPU and GPU processing times of the 2D SPECFEM package for different mesh sizes for elastic simulations with 15,000 time steps. An Intel Broadwell e5-2680v4 with 28 cores was used for the CPU tests, and a mesh decomposition (not included in processing time) over 28 slices to enable MPI runs was performed. A single Nvidia Pascal P100 was used for the GPU tests.

Additionally, the iterative FWI process requires thousands of wave propagation simulations. To obtain an image within an acceptable time, the SPECFEM software suite is used, which involves an optimized spectral-element solver that features support for multi Graphics Processing Unit (GPU) computation. Because of this, simulation time is significantly reduced, as illustrated in FIG. 4.

Measurements

Solving non-convex optimization problems with local optimization tools does not ensure convergence to the exact solution. In geophysical FWI, differences between observed and simulated waveforms, whether they are pressure records offshore or ground motion records on shore, are often used to define a measure of misfit. This intuitively simple definition of misfit is by no means the only option, and other definitions frequently lead to faster convergence. Additionally, the choice of misfit should also be motivated by the parameters that one is trying to constrain, e.g., variations in wavespeed are generally best constrained by measurements involving differences between observed and simulated times of flight or "traveltimes." In this section, how the optimization problem is formulated and how data are transformed to maximize chances of success for global convergence are described.

Waveform Difference

The least-squares waveform cost function is defined as follows:

$$F_W(m) = \frac{1}{2}\sum_{r=1}^{N_{rec}} \int_0^T |p_{obs}(x_r, t) - p_{syn}(x_r, t, m)|^2 dt \quad (18)$$

wherein $F_W(m)$ is a sum of the residuals between the synthesized data, $p_{syn}(x_r, t, m)$, and the converted acoustic or (an)elastic wave data, $p_{obs}(x_r, t)$, over $N_{rec}$ number of the receiving transducers r at $x_r$, over a time window T, wherein m are the maps of selected parameters.

This formulation seeks to invert the entirety of available data, containing the maximum amount of information. Under perfect experimental conditions, very accurate reconstructions are possible, as shown in the next section.

Under real conditions, this cost function can be used only if the response of the transducer is perfectly characterized. In addition, the cycle-skipping condition has to be satisfied. It implies that the time of flight difference between observed and synthetic waves has to be less than half the period of the wave. If not, the inversion process might become trapped in a local minimum. In practice, this requires careful selection of a suitable frequency band.

Traveltime

To reduce the risks of getting trapped in a local minimum, other cost functions can be considered. A common strategy is to extract a property from the data that is easier to recover, using a mathematical transformation. For instance, it may be difficult to characterize the exact waveform that is generated by a transducer or by an array of transducers. In that case, using a waveform cost function may lead to an erroneous result, because of improper modeling. In contrast, the difference in time of flight between observed and synthetic data is less sensitive to the specifics of the transducer. We define the least-square traveltime cost function:

$$F_T(m) = \frac{1}{2}\sum_{r=1}^{N_{rec}} |T_{obs}(x_r) - T_{syn}(x_r)|^2$$

where $T_{obs}(x_r)$ represents the observed time of flight of the wave from the emitting source to the receiving point $x_r$.

This cost function can also be used in the first stage of the inversion process. By doing so, the resulting model that respects the time of flights will be less likely to generate cycle skipping. This model can be used as an initial model for the second stage of inversion involving a waveform cost function.

Instantaneous Phase

Following, the instantaneous phase $\psi(t)$ of the data $p(t)$ is considered, which may be obtained based on the transformation $$\psi(t) = \arctan\frac{\mathcal{J}(\tilde{p}(t))}{\mathcal{R}(\tilde{p}(t))}$$

Where $$\tilde{p}(t) = p(t) + \frac{i}{\pi}P\int_0^T \frac{p(t')}{t-t'}dt'$$

Here P denotes the Cauchy principal value.

A least-squares cost function based on the difference between the observed and synthetic instantaneous phase can be defined:

$$F_{IP}(m) = \frac{1}{2}\sum_{r=1}^{N_{rec}} \int_0^T |\psi_{obs}(x_r, t) - \psi_{syn}(x_r, t, m)|^2 dt \quad (11)$$

wherein $F_{IP}(m)$ is a sum of the residuals between the IP of synthesized data, $\psi_{syn}(x_r, t, m)$, and the IP of converted acoustic wave data, $\psi_{obs}(x_r, t)$, over $N_{rec}$ number of the receiving transducers r at $x_r$, over a time window T, wherein m are the maps of selected parameters.

This cost function is likely to be more convex than the waveform cost function, and thus the chances of successful inversion are considerably enhanced.

Double Difference

In practical acquisitions, uncertainties regarding the emitted waveform, its starting time, or the spatial positioning of the transducers can negatively affect reconstruction of the model. To ameliorate these source uncertainties, a powerful "double difference" measurement technique has been introduced. Instead of considering differences between synthetic and observed data, the double difference technique focuses on differential measurements between pairs of transducers, that is differences between differential measurements. This approach can be used for any kind of measurements, such as waveforms or traveltimes.

As an illustration, a differential traveltime measurement between two stations i and j is considered, which is obtained using the following criterion:

$$\Delta t_{ij}(p) = \operatorname*{argmax}_{i,j} \Gamma_{ij}(p, \tau) \text{ with } \Gamma_{ij}(p, \tau) = \int_0^T p(x_i, t+\tau)p(x_j, t)dt \quad (12)$$

The related double difference cost function is defined as $$F_{DD}(m) = \frac{1}{2} \sum_{r=1}^{N_{rec}} \sum_{j>i}^{N_{rec}} |\Delta t_{ij}(p_{obs}) - \Delta t_{ij}(p_{syn}(m))|^2 \quad (13)$$

wherein $F_{DD}(m)$ is a sum of the residuals between the synthetic time of flight difference $\Delta t_{ij}(p_{syn}(m))$, and the converted acoustic wave data time of flight difference $\Delta t_{ij}(p_{obs})$, between each pair from the $N_{rec}$ receiving transducers, wherein m is the maps of selected parameters. This cost function involves $$\binom{N_{rec}}{2}$$

measurements, which can be computed with the same computational cost as the cost functions defined by equations (10) and (11).

Hybrid Cost Function

Several cost functions are described, each with their own merits and demerits. In practice, one combines the advantages of each cost function and limit their drawbacks by formulating a hybrid cost function, e.g.

$$F_H(m) = \alpha F_T(m) + \beta F_{DD}(m) + \gamma F_{IP}(m) + \delta F_W(m) \quad (13)$$

with suitably chosen weights $\alpha$, $\beta$, $\gamma$ and $\delta$. Initially, one can focus on the traveltime terms $F_T(m)$ and $F_{DD}(m)$ and progressively switch to the instantaneous phase cost function $F_{IP}(m)$, followed by the waveform cost function $F_W(m)$. It has been shown that a hybrid inversion leads to a better minimization of each term of the hybrid cost function compared to minimizing each term separately based on independent inversions.

Multi-Scaling

To further improve spatial resolution, measurements involving different frequency bands are considered. Because low frequencies are less subject to attenuation and diffraction, they tend to be less noisy and less influenced by smaller-scale variations in the model. The associated inverse problem is thus more convex, but has a less spatial resolution. To improve this, one progressively increases the frequency content with each iteration, to ensure global convergence and accuracy of the reconstructed model.

Multi-Tapering

For dispersive signals, such as surface waves, it can be highly beneficial to measure frequency-dependent phase (traveltime) and amplitude anomalies using multi-tapering. This strategy is commonly used in earthquake seismology, but is less important for the predominant body waves used in ultrasonic imaging. Nevertheless, these tools have been developed and may be added to the arsenal of measurement techniques and strategies.

Ultrasound Data

It has been seen that the mathematical formulation of the inverse problem and the frequency band can strongly affect convergence of the algorithm. In this section, the important roles of a careful signal characterization and data acquisition geometry are demonstrated.

Selection of the Frequency Band

As mentioned previously, a priori knowledge is required to select the operating band of frequencies of the system. In conventional B-mode imaging ultrasound systems, this band is chosen to be as high as possible, provided the signal-to-noise ratio is considered correct. In the FWI approach, the level of non-linearity of the underlying optimization problem is directly proportional to the level of the band of frequencies that is used in the real experiment. If this frequency content is too high, it may be impossible to obtain an image using FWI, even with noiseless data.

1) Waveform Cost Function

The problem can be solved when at least a part of the frequency content of the purely refracted wavefront signatures respect the cycle skipping condition:

$$|t_{obs} - t_{syn}| < \frac{1}{2F}$$

where $t_{obs} - t_{syn}$ models the difference in time of flight between an observed wavefront and its synthetic counterpart, and F represents the frequencies contained in the data. The band of frequencies respecting the cycle skipping condition must be large enough to generate a wavefront that is smaller than the medium to image. The maximum limit $F_{max}$ should be chosen depending on the computational resources available and the chosen algorithm.

In practice, the band of frequencies may be chosen depending on a priori knowledge of the acoustic properties of the medium. These properties, such as the wavespeeds and attenuation, are directly controlling the time of flight t. Consequently, it is the initial discrepancy between the numerical model of these parameters and reality that will drive the difference $t_{obs} - t_{syn}$. In medical imaging, for instance, these acoustic properties are well known for each tissue, but the dimensions and the positioning of the tissues may vary from one patient to another. Depending on these uncertainties, it is possible to determine the largest difference $t_{obs} - t_{syn}$ that may appear during the inversion.

a) Deterministic Approach

One can determine the appropriate bandwidth with the following formula:

$$\begin{cases} F_{min} + \Delta F < \underset{i,j}{\mathrm{argmax}} \int_{x_{s_i}}^{x_{r_j}} \left| \frac{1}{c_{init}(x)} - \frac{1}{c_{init}(x) + \Delta c(x)} \right| dx \\ \frac{\overline{c_{init}}}{F_{min}} \propto L \text{ or } \exists\, s(t) \text{ such that} \\ \left\{ \begin{array}{c} F_{min}(s(t)),\, F_{max}(s(t)) \in [F_{min};\, F_{min} + \Delta F], \\ env(s(t))\overline{c_{init}} < L \end{array} \right\} \end{cases}$$

where $F_{min}$ is the minimum frequency, $\Delta F$ is the width of the frequency band that respects the cycle skipping condition, $x_{s_i}$ the position of the $i^{th}$ source, $x_{r_j}$ the position of the $j^{th}$ receiver, $c_{init}(x)$ the initial guess of the wavespeed at position x, $\Delta c(x)$ the initial uncertainty about the wavespeed at position x, $\overline{c_{init}}$ the mean of the initial guess wavespeed in the medium, L the minimum dimension of the medium, s(t) a pulse signal, and env( ) the envelope function.

It is also worth noting that accurately identifying the maximum potential wavespeed discrepancies helps to select a higher frequency band, which leads to better resolution.

b) Empirical Approach

When uncertainties are large, or the medium to image is totally unknown, the deterministic approach may not apply, and the frequency content may be chosen with an empirical approach based on observed data, combined with a sweep in frequency. If the selected frequency band is too low, purely refracted wavefront signatures of the observed data should look similar to the purely refracted wavefront signatures of the synthesized data. If the selected frequency band is too high, purely refracted wavefront signatures of the observed data should be temporally located far from the purely refracted wavefront signatures of the synthesized data, or may not be identifiable.

When sweeping from low to high frequencies, the correct frequency to choose would be the one that starts to show visible discrepancies between observed and synthesized wavefronts, but such that the cycle skipping condition is still respected. This ensures that the observed data contains valuable information with respect to the inversion process. It is worth noting that this approach can be automated with an algorithm.

2) Traveltime Cost Function

In the case of a traveltime cost function, an empirical approach based on frequency sweeping is possible. A priori knowledge about the medium is not necessary, but helps to reduce the required frequency band for the frequency sweep. The approach used for a waveform cost function also applies, but the traveltime approach is not limited by the cycle skipping condition.

In practice, the only constraint is to make sure that purely refracted wavefront signatures remain identifiable. When increasing the frequency content, diffraction effects may affect our ability to distinguish diffracted from refracted wavefronts, which affect the algorithm, when computing the traveltime differences. This approach can also be automated.

Acquisition Geometry

The acquisition geometry strongly affects image quality. Here several available options are discussed.

One-Sided Acquisition

Figure 5:
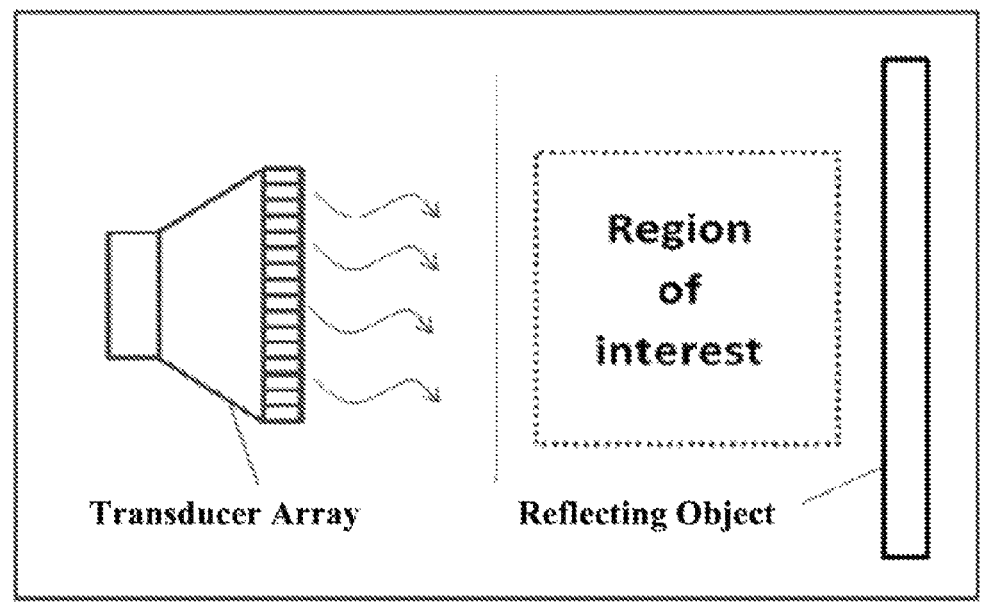
FIG. 5 shows an example of a one-sided acquisition setup.

In conventional echography, the same transducer array is used to send a pulse and to record its echoes. This configuration primarily enables recording of reflected waves, which, according to the geophysics literature, contain less invertible data than transmitted waves. To avoid an inversion based only on reflected waves with a single transducer array, the experimental setup illustrated in FIG. 5 is considered, featuring a reflector located behind the region of interest. Its position with respect to the emitting transducer array is known and part of the initial model. The recording duration of the transducer array has to be long enough to facilitate recording of waves reflected by the reflector.

Multi-Sided Acquisition

A more natural way to capture transmitted waves is to use a second transducer array placed at a different location from the first transducer array. For example, the second transducer array may be placed at the opposite side of the first transducer array. The relative position between the two transducer arrays must be known. Compared to the one-sided acquisition, this setup increases the amplitude of the recorded waves and reduces the difficulty of the inverse problem, because waves are less affected by the medium.

To maximize the amount of information, acquisitions may be repeated and performed using different emitted signals and variable array geometries or element positions.

Acquisition by Submersion in Water

Water is a homogeneous acoustically perfectly characterized medium. For medical imaging, using an acquisition setup with transducer arrays and (parts of) the body immersed in water, or other liquids, presents the following opportunities. In some embodiments, the medium is de-ionized and/or de-aerated water. One has complete control over the geometry of the emitting and receiving transducers and elements, which do not have to be attached to the skin. From a modeling perspective, this is highly desirable, because the recording geometry is known very precisely. Because the wavespeed and the mass density of the body and the liquid are very similar, it is straightforward to jointly model wave propagation in the immersion fluid and the body. Instead of modeling the behavior of the transducer array when emitting a wave, it is sufficient to characterize the incident wave on the body. This simplifies the initialization of the wave propagation solver.

Emitted Transducer Signal

As described previously, the choice of frequency band depends on the nature of the region of interest and on the cost function used to solve the inverse problem. In medical imaging, for regions of interest that do not contain bones or fat tissue, the range values of model parameters are small enough to enable an accurate resolution fitting the bandwidth of a piezoelectric transducer. For such problems, relevant emitted signals involve a transient pulse and a narrow bandwidth (typically [0.5 f; 1.5 f], where f is the central frequency). An example is a Ricker wavelet. Its central frequency should be chosen high enough to enable spatial resolution, and small enough to enable convergence to the global minimum.

If higher parameter contrasts are involved, as encountered when the region of interest contains bones or fat tissue, or in non-medical applications (e.g., NDT), a wider band of frequencies is necessary (typically [f; 10 f]). Data may be acquired using a single large bandwidth and a transient signal, using, for instance, a CMUT device. Alternatively, one can conduct a series of acquisitions using different transient signals, involving different bands of frequencies generated by various piezoelectric transducers, or a single CMUT device.

Model Parameterization

Wave propagation is influenced by different physical parameters, such as compressional and shear wavespeeds, density, attenuation, anisotropy or poroelastic coefficients. The "model" m is a combination of maps of these parameters that have to be chosen depending on the nature of the image target. Choosing the entire set of parameters may lead to an incorrect solution, and may have a prohibitive computational cost.

For the simplest isotropic elastic case, the gradient takes the form $$\delta F = \int_\Omega (\delta \ln \rho K_\rho + \delta \ln \kappa K_\kappa + \delta \ln \mu K_\mu) d\Omega \tag{14}$$

where $\mu$ denotes the shear modulus (which vanishes in a gas or liquid). For anelastic, isotropic simulations the misfit gradient takes the form $$\delta F = \int_\Omega (\delta \ln \rho K_\rho + \delta \ln \kappa K_\kappa + \delta \ln \mu K_\mu + \delta Q^{-1} K_{Q^{-1}}) d\Omega \tag{15}$$

where the quality factor Q represents attenuation.

In fat tissue, attenuation effects are dominant. The value of the quality factor Q is known, but, depending on the patient, the size and shape of the fat tissue may change, and cannot be easily characterized prior to inversion. Even if the region of interest does not include such tissue, it is likely that the wave, generated by an external transducer array, traverses fat tissue. Thus, to obtain a sharp reconstruction of tissue located under fat, incorporating attenuation in the model is relevant. Attenuation may also be relevant in non-medical applications.

More complex parameterizations involving seismic anisotropy are readily accommodated. For example, in earthquake seismology, one routinely uses transversely isotropic parameters, which involves five elastic parameters. In medical imaging, bones exhibit anisotropy. In NDT, composite materials have anisotropy as well.

Numerical Experiments

To illustrate ultrasonic FWI, different numerical wavespeed maps for reconstruction from synthetic data are created. To perform accurate numerical wave propagation simulations in heterogeneous and irregular media, the open source SPECFEM software package is used, which implements a spectral-element method in two or three dimensions. Multi-Graphics Processing Unit (GPU) support has been added in the two-dimensional case for this study and is also available in the three-dimensional case. Despite the large number of floating-point operations that need to be performed, between 1 and 4 GPUs suffice for the numerical experiments presented here.

Figures 6A, 6B, 6C, 6D, 6E, 6F, 6G:
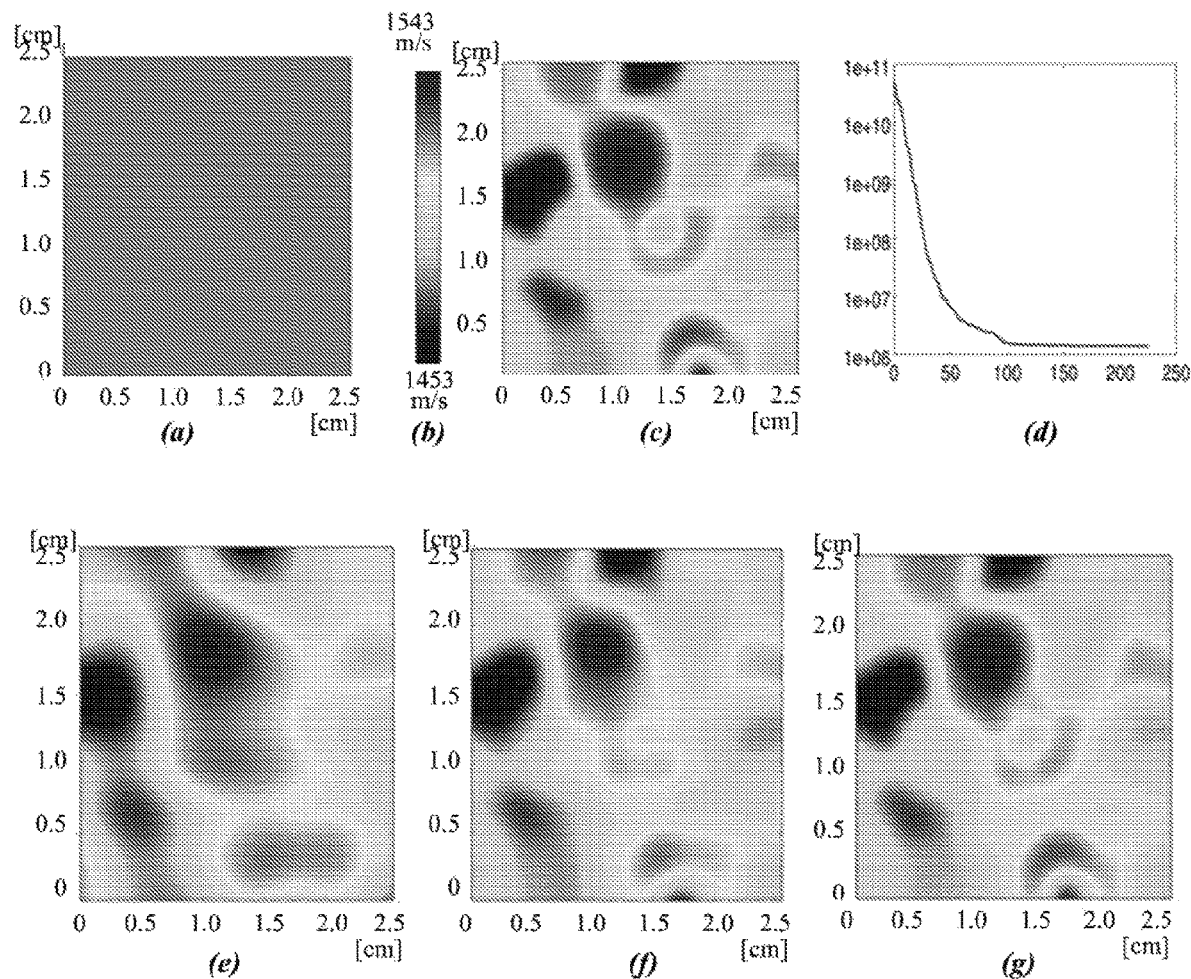
FIGS. 6(a), 6(b), 6(c), 6(d), 6(e), 6(f), 6(g) show reconstruction of a continuous wavespeed map using FWI and 4-plane wave illuminations (Experiment A). (a) Wavespeed map at the beginning of the process (homogeneous, 1,500 m/s); (b) Legend showing a colorbar of the wavespeed amplitude for each of the wavespeed maps (1453 to 1543 m/s); (c) Target map; (d) Evolution of the discrepancy between observed data, obtained from (c) and synthetic data obtained from the numerical model at each iteration; (e) Model after 10 iterations; (f) Model after 20 iterations; and (g) Final inverted model after 225 iterations.

Let us first consider the 2D plane-strain case. A 2.56 cm×2.56 cm acoustic medium with perfectly reflecting free boundaries is defined. Density is assumed to be constant, which is a reasonable assumption for weak-contrast media. The L-BFGS minimization algorithm combined with Wolfe conditions is used to minimize the waveform cost function, implemented based on the open source SeisFlows workflow [http://github.com/rmodrak/seisflows]. For the sake of generality and to demonstrate the power of the inversion toolkit, the initial wavespeed map shown in FIG. 6(a) is purposely chosen to be homogeneous with a value of 1,500 m/s. Synthetic data are simulated by sending a plane wave from one side of the medium and recording the transmitted wave on the other side. The process is repeated for each of the four sides of the medium. The transducer arrays are composed of 32 elements. In this experiment, only four plane waves are necessary, generated with a Ricker wavelet (i.e., the second time-derivative of a Gaussian) with a 1 MHz dominant frequency sent simultaneously by each transducer in the array. The salient qualities of this signal include its transitory nature, enabling good spatial resolution, and its relatively narrow-band spectrum, which matches the bandwidth of piezoelectric transducers.

The target wavespeed map shown in FIG. 6(c) in Experiment A was generated randomly and smoothed to only contain continuous wavespeed variations. The maximum variations with respect to the mean of 1,500 m/s are ±50 m/s, with wavespeed amplitudes shown by the colorbar in FIG. 6(b). The inversion process is performed over 225 iterations, and the cost function, shown in FIG. 6(d), decreases by four orders of magnitude between its evaluation for the initial model, shown in FIG. 6(a), and the inverted model (after 225 steps), shown in FIG. 6(g). FIGS. 6(e) and 6(f) show the inversion at 10 and 20 steps respectively. One observes that the cost function rapidly decreases during the first iterations, before exhibiting asymptotic behavior after a hundred iterations. The compute time for this simulation is around 45 minutes using one NVIDIA GPU Titan Black graphics card. To obtain this result, the duration of the simulation was limited to 1.7 ms of wave propagation, which is long enough to record the purely diffracted residual of the wave sent from the other side, and short enough to avoid recording reflected waves. Besides saving computing time, this approach makes the optimization problem more convex. Some remaining differences between the target and inverted maps are visible close to the edges of the medium, where the transducers are located, which is an area that exhibits very high sensitivity.

Figures 7A, 7B, 7C, 7D, 7E, 7F:
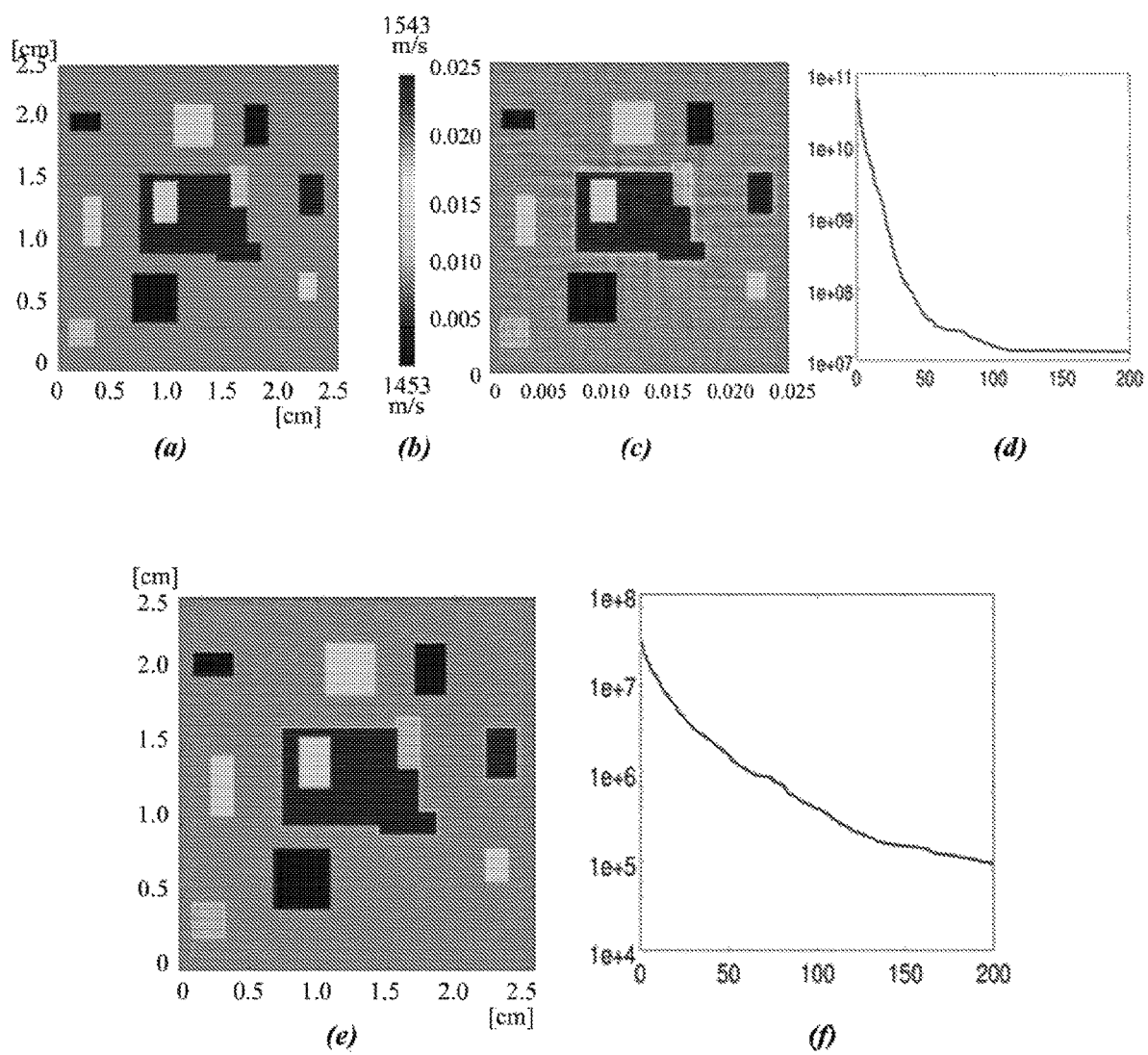
FIGS. 7(a), 7(b), 7(c), 7(d), 7(e), 7(f) show reconstruction of a discontinuous wavespeed map using FWI and 4-plane wave illuminations, starting with a homogeneous model (Experiment B). (a) Target model; (b) Legend showing a colorbar of the wavespeed amplitude for each of the wavespeed maps; (c) Inverted model 1; (d) Evolution of the discrepancy between observed data, obtained from (c) and synthetic data obtained from the numerical model at each iteration; (e) Inverted model 2; and (f) Evolution of the discrepancy between observed data and synthetic data, using (c) as a starting model and including reflected waves into the inversion.

The target map in Experiment B, shown in FIG. 7(a), involves various discontinuous variations within the medium. This problem is more difficult than Experiment A, because of diffractions created by discontinuities, and especially by sharp scatterers, make the inverse problem even more non-convex. The magnitude of the wavespeeds, and therefore velocity discontinuities can be seen in the colorbar, FIG. 7(b). Applying the same procedure as for the target map 6(c) of Experiment A, the inverted model shown in FIG. 7(c) with correct global shapes is obtained. Nevertheless, visible oscillations appear in the inverted model, and the cost function 7(d) decreases by three orders of magnitude, i.e., less than in Experiment A. To obtain a better result, a second step is added to the inversion procedure, with a different experimental setup: for each of the four simulations, the transducer array that emits the plane wave also records pressure, and the duration of the wave propagation simulation is doubled, such that the wave sent by this transducer has enough time to cross the medium twice and can thus be recorded by the emitting transducer array as well. The inverted model shown in FIG. 7(c) is used as the initial model for the new inversion process. With this procedure, more data have to be inverted, which explains the discontinuous value between the cost function shown in FIG. 7(d) at its last iteration and the cost function at the first iteration, shown in FIG. 7(f). The new cost function decreases by two orders of magnitude. The final inverted model shown in FIG. 7(e), does not contain oscillations and is closer to the target model. In the numerical tests, attempting to minimize the total amount of data at once led to a local minimum far away from the correct target map, which confirms the importance of performing the inversion with transmitted waves first, and then gradually adding reflected wave content. For the entire inversion, around 400 iterations were necessary, which lasted about 2.5 hours using a single NVIDIA Titan Black GPU.

Figures 8A, 8B, 8C, 8D:
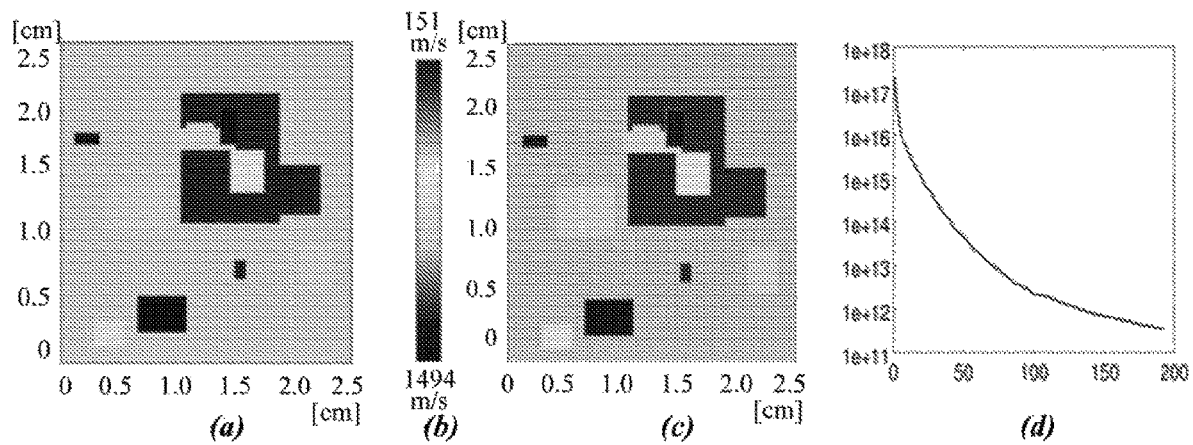
FIGS. 8(a), 8(b), 8(c), 8(d) show reconstruction of a very low contrast wavespeed map, using a 5 MHz dominant frequency Ricker signal, 4-plane wave illuminations, and a homogeneous initial model (1,500 m/s) (Experiment C). (a) Target model; (b) Legend showing a colorbar of the wavespeed amplitude for each of the wavespeed maps (1494 to 1510 m/s); (c) Inverted model; and (d) Evolution of the discrepancy between observed data and synthetic data.

The target map of Experiment C, shown in FIG. 8(a), is similar to model 7(a) of Experiment B, but with weaker contrasts. The colorbar in FIG. 8(b) illustrates the amplitude of the wavespeeds for the model. The purpose of this model reconstruction test is to show the feasibility of a high-frequency inversion, in order to fit frequencies of echography scanner arrays used in practice. Here, the dominant frequency of the Ricker wavelet is 5 MHz. The same source-receiver configuration setup as in Experiment A is used. In the inverted map 8(c), various structures are properly reconstructed, with the even sharper reconstruction of the edges, due to the smaller wavelength of the emitted waves. As at the end of the first stage of Experiment B, oscillations are visible, which could be removed using the same second stage process as in Experiment B. One can also observe that the cost function shown in FIG. 8(d) starts with a higher initial value than in previous experiments, because of the higher dominant frequency of the signal, and that it decays by six orders of magnitude between the initial model and the final iteration.

Figure 9:
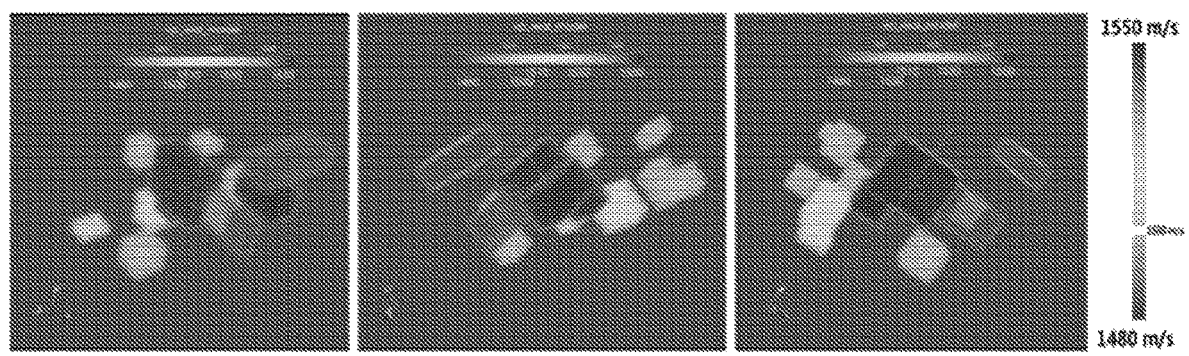
FIG. 9 shows perspective views of the target 3D wavespeed map (Experiment D). For readability, the color of the background speed (1500 m/s) is transparent to show various heterogeneities.
Figure 10:
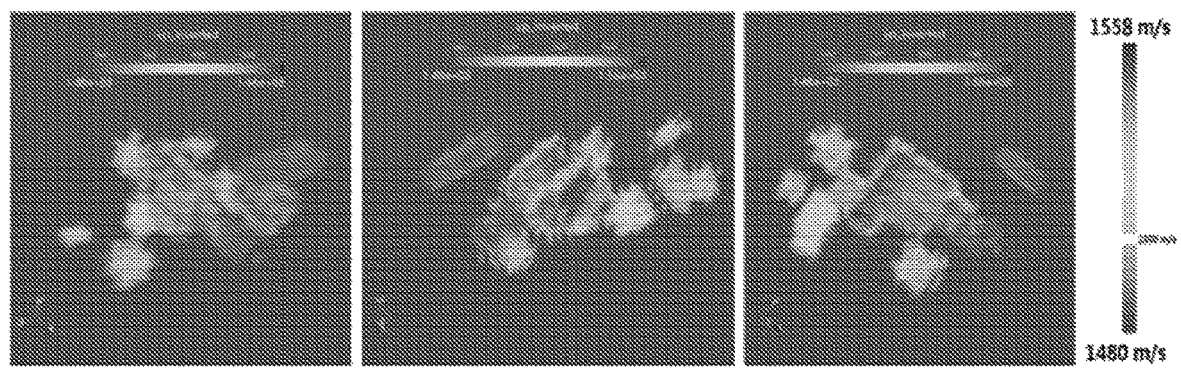
FIG. 10 shows perspective views of the reconstructed 3D wavespeed map results (Experiment D).

Next, the 3D case is considered. In Experiment D, a 3D map is used, which is a 3D version of the 2D model used in Experiment B. The model to reconstruct in FIG. 9 is a cube with edges of 2.56 cm. The three images display the same model from different viewpoints. The source-receiver setup is composed of two 32×32 transducers arranged as a matrix, which are able to emit and record from a side of the cube. A plane wave is emitted and recorded on the opposite side. Only four of the six possible combinations of source-receiver acquisitions are used to perform the inversion, in order to limit the computation time. The initial model is a homogeneous cube with a 1500 m/s wavespeed value. The reconstructed map for Experiment D is presented in FIG. 10 with the same three viewpoints as the target model of FIG. 9. The inversion reconstructs the same heterogeneities as the target model, with each block consisting of homogeneous wavespeed values. One can see some perturbations close to their edges, even if the discontinuities remain identifiable.

Between the initial and inverted models, the cost function decreased by ten orders of magnitude. The inversion process took around 600 iterations and lasted 20 hours using 4 NVIDIA K20 graphics cards.

Ultrasound FWI may be used to reconstruct continuous and discontinuous wavespeed maps. The FWI process has been adapted to realistic ultrasound acquisitions such as narrow-band piezoelectric transducer arrays. Only four plane wave illuminations are necessary to reconstruct 2D/3D maps. In addition, due to a waveform cost function formulation of the problem, the inversion process is standalone, and neither manual nor automated phase selection is required during the inversion. The computation time has been kept reasonable because of the use of GPUs, despite the thousands of spectral-element simulations required for the calculation of a single image.

The conventional echography acquisition setup is adapted to fit constraints of non-convex optimization by adding a second transducer array located behind the medium to record transmitted waves, in addition to reflected waves. Another important difference compared to the conventional echography acquisition setup is related to the choice of the frequency band. In conventional echography, which aims to identify the temporal position of the echoes as a spatial position, a highly transient signal is preferred, leading to the use of the highest possible frequencies, within the limits permitted by attenuation. In Full Waveform Inversion, the frequencies are also constrained by the non-convexity of the problem, which tends to be higher when using higher frequencies. Thus, the selected frequency band must be a trade-off between ensuring spatial resolution and ensuring resolvability of the inverse problem. In the waveform cost function case, this requires incorporation of some a priori knowledge about potential gaps between real and expected values of parameters for the whole wavespeed map to estimate the most suitable frequency band. An initial estimation of the maps of parameters is a necessary input to start the FWI process. This initial model may reflect basic a priori knowledge about the medium, with the goal of maximizing the chances of convergence of the algorithm. For instance, when the embodiment involves specific parts of the body, the initial model may be chosen using the usual shapes of the tissues, and the usual values of the physical parameters in these tissues. It is also worth knowing the minimum and maximum values these parameters may take. Knowing the maximum possible distance between the current model and the true model may help to select the appropriate band of frequencies of the emitted signal. For instance, when performing a wavespeed inversion, knowing the potential range of wavespeeds may help assess—and thereby limit—potential traveltime differences between observed and synthetic data. If a waveform cost function is used, this traveltime difference has to respect the cycle skipping condition that links traveltimes and frequencies of the emitted signal. The frequency band should be selected to obey the cycle skipping condition.

Definitions

In this document, acoustic waves and (an)elastic waves are referred to as the mechanical waves in gases/liquids and in solid media, respectively.

The terms "arrays" "transducer" and "transducer array" are synonymous, unless the context dictates otherwise. The term "element" as used herein refers to a transducer element that is a transmitting element capable of emitting ultrasonic signals or a receiving element capable of capturing ultrasonic signals propagated through a medium. A transducer or a transducer array may include transmitting element(s) and/or receiving element(s).

Reference throughout this specification to "one embodiment", "an embodiment", "some embodiments", or similar language means that a particular feature, structure, or characteristic described in connection with the indicated embodiment is included in at least one embodiment of the present solution. Thus, the phrases "in one embodiment", "in an embodiment", "some embodiments", and similar language throughout this specification may, but do not necessarily, all refer to the same embodiment.

The use of the word "a" or "an," when used in conjunction with the term "comprising" in the claims and/or the specification may mean "one," but it is also consistent with the meaning of "one or more," "at least one, "and "one or more than one."

The term "(s)" following a noun contemplates the singular or plural form, or both.

The terms "and/or" or "/" means any one of the items, any combination of the items, or all of the items with which this term is associated.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

When used in this document, the term "exemplary" is intended to mean "by way of example" and is not intended to indicate that a particular exemplary item is preferred or required.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

All of the methods and apparatus disclosed and claimed herein can be made and executed without undue experimentation in light of the present disclosure. While the invention has been described in terms of preferred embodiments, it will be apparent to those having ordinary skill in the art that variations may be applied to the apparatus, methods, and sequence of steps of the method without departing from the concept, spirit, and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope, and concept of the invention as defined.

What is claimed is:

1. A system for producing ultrasound images, comprising:
    a transmitting element that emits a signal having a band of frequencies specified by a priori knowledge of a medium and an image reconstruction algorithm, wherein the transmitting element has a known and controlled location within the system, and wherein the medium comprises an animal tissue or a non-human object;
    a receiving element that captures acoustic/(an)elastic waves that are emitted by the transmitting element and that are transmitted through and reflected from the medium, wherein the receiving element has a lateral extent smaller than a wavelength of the waves in the medium and a known and controlled location within the system;

a processor; and a non-transitory computer readable medium containing programming instructions that, when executed, cause the processor to:

convert the captured acoustic/(an)elastic waves into observed imaging data;

perform a Full Waveform Inversion process in a time domain on the observed imaging data against synthesized data derived from a simulated model of the observed imaging data using a wave propagation solver;

use the synthesized data to generate image representations of the medium; and store or display the image representations of the medium.

2. The system of claim 1, further comprising one or more additional receiving elements located at a different position from the transmitting element that captures the acoustic/(an)elastic waves that are transmitted through the medium.

3. The system of claim 1 or 2, wherein the programming instructions for performing the Full Waveform Inversion process further comprises programming instructions that, when executed, cause the processor to perform three-dimensional acoustic or viscoacoustic simulations.

4. The system of claim 1 or 2, wherein the programming instructions for performing the Full Waveform Inversion process further comprises programming instructions that, when executed, cause the processor to perform three-dimensional elastic or anelastic simulations.

5. The system of claim 1, wherein the programming instructions for performing the Full Waveform Inversion process further comprises programming instructions that, when executed, cause the processor to invert low-frequency content of the observed imaging data followed by progressively adding higher frequency content of the observed imaging data.

6. The system of claim 1, wherein the programming instructions further comprise programming instructions that, when executed, cause the processor to smooth the simulated model.

7. The system of claim 6, wherein the programming instructions for smoothing the simulated model further comprise programming instructions that, when executed, cause the processor to smooth the simulated model by a Gaussian smoothing process.

8. The system of claim 1, wherein the programming instructions further comprise programming instructions that, when executed, cause the processor to generate the image representation of the medium that is a physical three-dimensional model.

9. The system of claim 1, wherein the programming instructions further comprise programming instructions that, when executed, cause the processor to generate the image representation of the medium that is immersed in a liquid.

10. The system of claim 1, wherein the programming instructions further comprise programming instructions that, when executed, cause the processor to generate the image representation of the medium that is immersed in water.

11. The system of claim 1, wherein the programming instructions for performing the Full Waveform Inversion process further comprises programming instructions that, when executed, cause the processor to:

(i) provide an initial physical model;

(ii) determine the synthesized data, by a computer, by simulating wave propagation through the physical model;

(iii) back-propagate adjoint source terms determined by a cost function based on a comparison of the synthesized data and the converted acoustic/(an)elastic wave data to update the physical model; and (iv) repeat (ii) and (iii) until the residual between the synthesized data and the converted acoustic/(an)elastic wave data is less than a predetermined threshold.

12. The system of claim 1, wherein the animal tissue is a human tissue.

13. The system of claim 1, wherein the medium is an object being non-destructively tested (NDT) and the image representations of the medium comprise internal or external structural details of the object or speed of sound or attenuation in the medium.

14. A method of producing a set of ultrasound images, the method comprising:

emitting, by a transmitting element, a signal having a band of frequencies specified by a priori knowledge of a medium and the image reconstruction algorithm, wherein the transmitting element has a known and controlled location within a system, and wherein the medium comprises an animal tissue or a non-human object;

capturing, by a receiving element, acoustic/(an)elastic waves that are emitted by the transmitting element and that are transmitted through and reflected from the medium, wherein the receiving element has a lateral extent smaller than a wavelength of the waves in the medium and a known and controlled location within the system;

converting the captured acoustic/(an)elastic waves into observed imaging data;

performing a Full Waveform Inversion process in a time domain on the observed imaging data against synthesized data derived from a simulated model of the observed imaging data using a wave propagation solver;

using the synthesized data to generate image representations of the medium; and storing or displaying image representations of the medium.

15. The method of claim 14, further comprising:

capturing, by one or more additional receiving elements located at a different location from the transmitting element, the acoustic/(an)elastic waves that are transmitted through the medium.

16. The method of claim 14 or 15, wherein performing the Full Waveform Inversion process further comprises performing three-dimensional acoustic or viscoacoustic simulations.

17. The method of claim 14 or 15, wherein performing the Full Waveform Inversion process further comprises performing three-dimensional elastic or anelastic simulations.

18. The method of claim 14, wherein performing the Full Waveform Inversion process comprises inverting low-frequency content of the observed imaging data followed by progressively adding higher frequency content of the observed imaging data.

19. The method of claim 14, further comprising smoothing the simulated model.

20. The method of claim 19, wherein smoothing the simulated model comprises applying a Gaussian smoothing process to the simulation model.

21. The method of claim 14, wherein the image representations of the medium is a physical three-dimensional model.

22. The method of claim 14, wherein the medium is an object being non-destructively tested (NDT) for quality assurance/quality control (QA/QC) or for measurement purposes.

23. The method of claim 14, wherein capturing the acoustic waves further comprises immersing the medium in a liquid.

24. The method of claim 23, wherein the liquid is water.

25. The method of claim 14, wherein performing the Full Waveform Inversion process comprises:
   (i) providing an initial physical model;
   (ii) determining the synthesized data, by a computer, by simulating wave propagation through the physical model;
   (iii) back-propagating adjoint source terms determined by a cost function based on a comparison of the synthesized data and the converted acoustic/(an)elastic wave data to update the physical model; and
   (iv) repeating (ii) and (iii) until the residual is less than a predetermined threshold.

26. The method of claim 25, wherein the cost function is a waveform cost function, an expression of the waveform cost function comprising:

$$F_W(m) = \frac{1}{2} \sum_{r=1}^{N_{rec}} \int_0^T \left| p_{obs}(x_r, t) - p_{syn}(x_r, t, m) \right|^2 dt,$$

wherein $F_W(m)$ is a sum of the residuals between the synthesized data, $p_{syn}(x_r, t, m)$, and the converted acoustic/(an)elastic wave data, $p_{obs}(x_r, t)$, over $N_{rec}$ number of the receiving transducers r at $x_r$, over a time window T, wherein m are the maps of selected parameters.

27. The method of claim 25, wherein the cost function is a traveltime cost function, an expression of the traveltime cost function comprising:

$$F_T(m) = \frac{1}{2} \sum_{r=1}^{N_{rec}} |T_{obs}(x_r) - T_{syn}(x_r, m)|^2,$$

wherein $F_T(m)$ is a sum of the residuals between the synthetic time of flight, $T_{syn}(x_r, m)$, and the time of flight of converted acoustic/(an)elastic wave data, $T_{obs}(x_r)$, over $N_{rec}$ number of the receiving transducers r at $x_r$, wherein m are the maps of selected parameters.

28. The method of claim 25, wherein the cost function is an instantaneous phase (IP) cost function, an expression of the instantaneous phase cost function comprising:

$$F_{IP}(m) = \frac{1}{2} \sum_{r=1}^{N_{rec}} \int_0^T |\psi_{obs}(x_r, t) - \psi_{syn}(x_r, t, m)|^2 dt,$$

wherein $F_{IP}(m)$ is a sum of the residuals between the IP of synthesized data, $\psi_{syn}(x_r, t, m)$, and the IP of converted acoustic/(an)elastic wave data, $\psi_{obs}(x_r, t)$, over $N_{rec}$ number of the receiving transducers r at $x_r$, over a time window T, wherein m are the maps of selected parameters.

29. The method of claim 25, wherein the cost function is a double difference cost function, an expression of the double difference cost function comprising:

$$F_{DD}(m) = \frac{1}{2} \sum_{r=1}^{N_{rec}} \sum_{j>i}^{N_{rec}} |\Delta t_{ij}(p_{obs}) - \Delta t_{ij}(p_{syn}(m))|^2,$$

wherein $F_{DD}(m)$ is a sum of the residuals between the synthetic time of flight difference $\Delta t_{ij}(p_{syn}(m))$, and the converted acoustic/(an)elastic wave data time of flight difference $\Delta t_{ij}(p_{obs})$, between each pair from the $N_{rec}$ receiving transducers, wherein m are the maps of selected parameters.

30. The method of claim 25, wherein the cost function is a hybrid cost function, an expression of the hybrid cost function comprising:

$$F_H(m) = \alpha F_T(m) + \beta F_{DD}(m) + \gamma F_{IP}(m) + \delta F_W(m),$$

Wherein $F_T(m)$ is the traveltime cost function, $F_{DD}(m)$ is the double difference cost function, $F_{IP}(m)$ is the instantaneous phase cost function and $F_W(m)$ is the waveform cost function, wherein $\alpha$, $\beta$, $\gamma$ and $\delta$ are weights of $F_T(m)$, $F_{DD}(m)$, $F_{IP}(m)$ and $F_W(m)$, respectively.

31. The method of claim 14, wherein the animal tissue is a human tissue.

32. The method of claim 14, wherein the medium is an object being non-destructively tested (NDT) and the image representations of the medium comprise internal or external structural details of the object or speed of sound or attenuation in the medium.

* * * * *